(12) United States Patent
Blais et al.

(10) Patent No.: US 9,422,345 B2
(45) Date of Patent: Aug. 23, 2016

(54) EXPRESSION SYSTEM

(75) Inventors: Normand Blais, Laval (CA); Philippe Marc Helene Dehottay, Rixensart (BE); Marianne Dewerchin, Rixensart (BE); Philippe Goffin, Rixensart (BE); Denis Martin, Laval (CA)

(73) Assignee: GlaxoSmithKline Biologicals S.A., Rixensart (BE)

( * ) Notice: Subject to any disclaimer, the term of this patent is extended or adjusted under 35 U.S.C. 154(b) by 1064 days.

(21) Appl. No.: 13/500,244

(22) PCT Filed: Oct. 7, 2010

(86) PCT No.: PCT/EP2010/065047
§ 371 (c)(1),
(2), (4) Date: Apr. 4, 2012

(87) PCT Pub. No.: WO2011/042516
PCT Pub. Date: Apr. 14, 2011

(65) Prior Publication Data
US 2012/0289688 A1   Nov. 15, 2012

(30) Foreign Application Priority Data

Oct. 8, 2009  (GB) .................................. 0917647.0

(51) Int. Cl.
*C07H 21/04* (2006.01)
*C07K 14/34* (2006.01)

(52) U.S. Cl.
CPC ........... *C07K 14/34* (2013.01); *C07K 2319/034* (2013.01)

(58) Field of Classification Search
CPC ...................................................... C07K 14/34
See application file for complete search history.

(56) References Cited

FOREIGN PATENT DOCUMENTS

| WO | 90/10015 | 9/1990 |
| WO | WO 2005/076010 | * 8/2005 |

OTHER PUBLICATIONS

Leong, et al., Cloned Fragment A of Diphtheria Toxin is Expessed and Secreted into the Periplasmic Space of *Escherichia coli* K12, Science 220:515-517 (1983).
Bishai, et al., High-Level Expression of a Proteolytically Sensitive Diphtheria Toxin Fragment in *Escherichia coli*, Journal of Bacteriology 169(11): 5140-5151 (1987).
O'Keefe and Collier, Cloned diphtheria toxin within the periplasm of *Escherichia coli* causes lethal membrane damage at low pH, Proc Natl Acad Sci 86: 343-346 (1989).
Titball, et al., Molecular Cloning and Nucleotide Sequence of the Alpha-Toxin (Phospholipase C) of Clostridium perfringens. Infection and Immunity 57(2): 367-376 (1989).
Humphreys, et al., High-Level Preiplasmic Expression in *Escherichia coli* Using a Eukaryotic Signal Peptide: Importance of Codon Usage at the 5' End of the Coding Sequence, Protein Expression and Purification 20: 252-264 (2000).

* cited by examiner

*Primary Examiner* — Albert Navarro
(74) *Attorney, Agent, or Firm* — Virginia G. Campen

(57) ABSTRACT

Polynucleotides are provided herein.

21 Claims, 16 Drawing Sheets

Lane 1: Molecular weights marker
Lane 2: BLR(DE3) strain non induced
Lane 3: BLR(DE3) strain induced
Lane 4: B834(DE3) strain non induced
Lane 5: B834(DE3) strain induced
Lane 6: HMS174(DE3) strain induced SDS PAGE: Novex TG 10-20%
Same samples loaded on A and B gels
A: Western blot revelation:
    Anti DTPa
    Anti mouse
    NBT-BCIP
B: Coomassie stained

Expression of CRM197 in bacterial cell (A) and in culture medium(B)

Gels showing induction of CRM197 3h 30°C
in different strains and solubility of expressed protein

Figure 7

Figure 7: CRM197 expression level in function of pH and temperature

LBT Buffered medium
( addition of 10% buffer K phosphate 1M, pH 7.5)
1. MW
2. 30° T0 cell
3. 30° T2 cell
4. 30° T4 cell
5. 30° Ton cell
6. 30° T4 medium
7. 30° Ton medium
8. 23° T2 cell
9. 23° T4 cell
10. 23° Ton cell
11. 23° T4 medium
12. 23° Ton medium

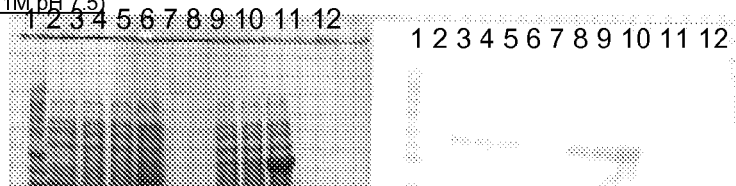

LBT Not Buffered medium
1. MW
2. 30° T0 cell
3. 30° T2 cell
4. 30° T4 cell
5. 30° Ton cell
6. 30° T4 medium
7. 30° Ton medium
8. 23° T2 cell
9. 23° T4 cell
10. 23° Ton cell
11. 23° T4 medium
12. 23° Ton medium

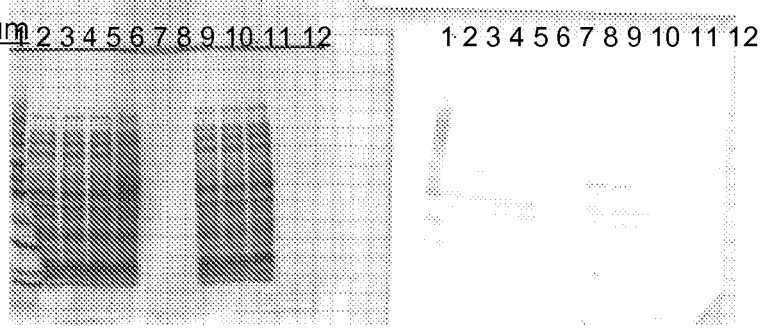

Coomassie stained gel     Western blot anti DTPa

Figure 9A

SEQ ID NO 1: Nucleotide sequence of the PhtE signal sequence
ATGAAATTTAGTAAAAAATATATAGCAGCTGGATCAGCTGTTATCGTATC
CTTGAGTCTATGTGCCTATGCA

SEQ ID NO 2: Amino acid sequence of the PhtE signal sequence
MKFSKKYIAAGSAVIVSLSLCAYA

SEQ ID NO 3: Nucleotide sequence of the SipA signal sequence
ATGAAAATGAATAAAAAGGTACTATTGACATCGACAATGGCAGCTTCGCT
ATTATCAGTCGCAAGTGTTCAAGCA

SEQ ID NO 4: Amino acid sequence of the SipA signal sequence
MKMNKKVLLTSTMAASLLSVASVQA

SEQ ID NO 5: Nucleotide sequence of the OmpA signal sequence
ATGAAAAAGACAGCTATCGCGATTGCAGTGGCACTGGCTGGTTTCGCTAC
CGTAGCGCAGGCC

SEQ ID NO 6: Amino acid sequence of the OmpA signal sequence
MKKTAIAIAVALAGFATVAQA

SEQ ID NO 7: Nucleotide sequence of the NspA signal sequence
ATGAAAAAAGCACTTGCCACACTGATTGCCCTCGCTCTCCCGGCCGCCGC
ACTGGCG

SEQ ID NO 8: Amino acid sequence of the NspA signal sequence
MKKALATLIALALPAAALA

SEQ ID NO 9: Nucleotide sequence of the TorT signal sequence
ATGCGCGTACTGCTATTTTTACTTCTTTCCCTTTTCATGTTGCCGGCATTTT
CG

Figure 9B

SEQ ID NO 10: Amino acid sequence of the TorT signal sequence
MRVLLFLLLSLFMLPAFS

SEQ ID NO 11: Nucleotide sequence of the SfmC signal sequence
ATGATGACTAAAATAAAGTTATTGATGCTCATTATATTTTATTTAATCATT
TCGGCCAGCGCCCATGCT

SEQ ID NO 12: Amino acid sequence of the SfmC signal sequence
MMTKIKLLMLIIFYLIISASAHA

SEQ ID NO 13: Nucleotide sequence of the FocC signal sequence
ATGATGAAGCACATGCGTATATGGGCCGTTCTGGCATCATTTTTAGTCTTT
TTTTATATTCCGCAGAGCTATGCC

SEQ ID NO 14: Amino acid sequence of the FocC signal sequence
MMKHMRIWAVLASFLVFFYIPQSYA

SEQ ID NO 15: Nucleotide sequence of the CcmH signal sequence
ATGAGGTTTTTATTGGGCGTGCTGATGCTGATGATCTCCGGCTCAGCGCTG
GCG

SEQ ID NO 16: Amino acid sequence of the CcmH signal sequence
MRFLLGVLMLMISGSALA

SEQ ID NO 17: Nucleotide sequence of the YraI signal sequence
ATGTCAAAACGAACATTCGCGGTGATATTAACCTTGTTGTGTAGCTTCTGT
ATTGGCCAGGCGCTTGCA

SEQ ID NO 18: Amino acid sequence of the YraI signal sequence
MSKRTFAVILTLLCSFCIGQALA

Figure 9C

SEQ ID NO 19: Nucleotide sequence of the TolB signal sequence
ATGATGAAGCAGGCATTACGAGTAGCATTTGGTTTTCTCATACTGTGGGCA
TCAGTTCTGCATGCT

SEQ ID NO 20: Amino acid sequence of the TolB signal sequence
MMKQALRVAFGFLILWASVLHA

SEQ ID NO 21: nucleotide sequence of the NikA signal sequence
ATGCTCTCCACACTCCGCCGCACTCTATTTGCGCTGCTGGCTTGTGCGTCT
TTTATCGTCCATGCC

SEQ ID NO 22: Amino acid sequence of the NikA signal sequence
MLSTLRRTLFALLACASFIVHA

SEQ ID NO 23: Nucleotide sequence of the FlgI signal sequence
ATGATTAAATTTCTCTCTGCATTAATTCTTCTACTGGTCACGACGGCGGCT
CAGGCT

SEQ ID NO 24: Amino acid sequence of the FlgI signal sequence
MIKFLSALILLLVTTAAQA

SEQ ID NO 25: Nucleotide sequence of the DsbA signal sequence
ATGAAAAAGATTTGGCTGGCGCTGGCTGGTTTAGTTTTAGCGTTTAGCGCA
TCGGCG

SEQ ID NO 26: Amino acid sequence of the DsbA signal sequence
MKKIWLALAGLVLAFSASA

SEQ ID NO:27: DNA sequence of MDSCRM1 primer
5' GCGCGGCATATGGGTGCGGATGATGTGGTGGATAGCAGC 3'

Figure 9D

SEQ ID NO:28: DNA sequence of MDSCRM2 primer

5' GCGGAGCTCGAGTTATTAGCTTTTGATTTCGAA 3'

SEQ ID NO:29: DNA sequence of primer

5' gga gcg cat atg att aaa ttt ctc tct gca tta att ctt cta ctg gtc acg acg gcg gct cag gct ggt gcg gat gat gtg gtg gat agc 3'

SEQ ID NO:30: DNA sequence of MDSCRM906NC primer

MDSCRM906NC primer
5' CAC GCC GCA TAG TTC GCA CCC GCA 3'

SEQ ID NO 31: Nucleotide sequence of the coding region of mature codon optimised CRM197

```
GGTGCGGATGATGTGGTGGATAGCAGCAAATCTTTTGTGATGGAAAACTTTAGCAGCTATCATGGCACCAAACCGGGCTA
TGTGGATAGCATTCAGAAAGGCATCCAGAAACCGAAAAGCGGCACCCAGGGCAACTATGATGATGATTGGAAAGAATTTT
ATAGCACCGATAACAAATATGATGCGGCGGGTTATAGCGTGGATAACGAAAATCCGCTGTCTGGCAAAGCGGGCGGTGTG
GTGAAAGTGACCTATCCGGGCCTGACCAAAGTGCTGGCCCTGAAAGTGCATAACGCGGAAACCATCAAAAAAGAACTGGG
CCTGAGCCTGACCGAACCGCTGATGGAACAGGTGGGCACCGAAGAATTTATTAAACGCTTTGGCGATGGCGCGAGCCGTG
TGGTTCTGAGCCTGCCGTTTGCGGAAGGCAGCAGCAGCGTGGAATATATTAACAACTGGGAACAGGCGAAAGCCCTGAGC
GTGGAACTGGAAATTAACTTTGAAACCCGTGGCAAACGTGGCCAGGATGCGATGTATGAATACATGGCGCAGGCGTGCGC
GGGCAATCGTGTGCGTCGTAGCGTGGGCAGCAGCCTGAGCTGCATTAACCTGGATTGGGACGTCATTCGTGATAAAACCA
AAACCAAAATCGAAAGCCTGAAAGAACATGGCCCGATCAAAAACAAATGAGCGAAAGCCCGAACAAAACCGTGAGCGAA
GAAAAAGCGAAACAGTATCTGGAAGAATTTCATCAGACCGCGCTGGAACATCCGGAACTGAGCGAACTGAAAACCGTGAC
CGGCACCAATCCGGTGTTTGCGGGTGCGAACTATGCGGCGTGGCGGTCAATGTGGCGCAGGTGATTGATAGCGAAACCG
CGGATAACCTGGAAAAAACCACCGCGGCCCTGAGCATTCTGCCGGGCATTGGCAGCGTGATGGGCATTGCGGATGGCGCG
GTGCATCATAACACCGAAGAAATTGTGGCGCAGAGCATTGCCCTGAGCAGCCTGATGGTGGCGCAGGCGATTCCGCTGGT
TGGCGAACTGGTGGATATTGGCTTTGCGGCGTACAACTTTGTGGAAAGCATCATCAACCTGTTTCAGGTGGTGCATAACA
GCTATAACCGTCCGGCGTATTCTCCGGGTCATAAAACCCAGCCGTTTCTGCATGATGGCTATGCGGTGAGCTGGAACACC
GTGGAAGATAGCATTATTCGTACCGGCTTTCAGGGCGAAAGCGGCCATGATATTAAAATTACCGCGGAAAACACCCCGCT
GCCCGATTGCGGGTGTTCTGCTGCCGACCATTCCGGGCAAACTGGATGTGAACAAAAGCAAAACCCATATTAGCGTGAACG
GTCGTAAAATTCGTATGCGTTGCCGTGCGATTGATGGCGATGTGACCTTTTGCCGTCCGAAAAGCCCGGTGTATGTGGGC
AACGGCGTGCACGCGAACCTGCATGTGGCGTTTCATCGTAGCAGCAGCGAAAAAATCCATAGCAACGAAATTAGCAGCGA
TAGCATTGGCGTGCTGGGCTATCAGAAAACCGTGGACCATACCAAAGTGAACTCTAAACTGAGCCTGTTCTTCGAAATCA
AAACC
```

Figure 9E

SEQ ID NO 32: Amino acid sequence of mature CRM197
GADDVVDSSKSFVMENFSSYHGTKPGYVDS
IQKGIQKPKSGTQGNYDDDWKEFYSTDNKY
DAAGYSVDNENPLSGKAGGVVKVTYPGLTK
VLALKVDNAETIKKELGLSLTEPLMEQVGT
EEFIKRFGDGASRVVLSLPFAEGSSSVEYI
NNWEQAKALSVELEINFETRGKRGQDAMYE
YMAQACAGNRVRRSVGSSLSCINLDWDVIR
DKTKTKIESLKEHGPIKNKMSESPNKTVSE
EKAKQYLEEFHQTALEHPELSELKTVTGTN
PVFAGANYAAWAVNVAQVIDSETADNLEKT
TAALSILPGIGSVMGIADGAVHHNTEEIVA
QSIALSSLMVAQAIPLVGELVDIGFAAYNF
VESIINLFQVVHNSYNRPAYSPGHKTQPFL
HDGYAVSWNTVEDSIIRTGFQGESGHDIKI
TAENTPLPIAGVLLPTIPGKLDVNKSKTHI
SVNGRKIRMRCRAIDGDVTFCRPKSPVYVG
NGVHANLHVAFHRSSSEKIHSNEISSDSIG
VLGYQKTVDHTKVNSKLSLFFEIKS.

SEQUENCE NO 33: Amino acid sequence of the PhtE signal sequence and the first 30 amino acids of CRM197
MKFSKKYIAAGSAVIVSLSLCAYAGADDVVDSSKSFVMENFSSYHGTKPGYV
DS

SEQ ID NO 34: Amino acid sequence of the Sip signal sequence and the first 30 amino acids of CRM197
MKMNKKVLLTSTMAASLLSVASVQAGADDVVDSSKSFVMENFSSYHGTKP
GYVDS

Figure 9F

SEQ ID NO 35: Amino acid sequence of the OmpA signal sequence and the first 30 amino acids of CRM197

MKKTAIAIAVALAGFATVAQAGADDVVDSSKSFVMENFSSYHGTKPGYVDS

SEQ ID NO 36: Amino acid sequence of the NspA signal sequence and the first 30 amino acids of CRM197

MKKALATLIALALPAAALAGADDVVDSSKSFVMENFSSYHGTKPGYVDS

SEQ ID NO 37: Amino acid sequence of the TorT signal sequence and the first 30 amino acids of CRM197

MRVLLFLLLSLFMLPAFSGADDVVDSSKSFVMENFSSYHGTKPGYVDS

SEQ ID NO 38: Amino acid sequence of the SfmC signal sequence and the first 30 amino acids of CRM197

MMTKIKLLMLIIFYLIISASAHAGADDVVDSSKSFVMENFSSYHGTKPGYVDS

SEQ ID NO 39: Amino acid sequence of the FocC signal sequence and the first 30 amino acids of CRM197

MMKHMRIWAVLASFLVFFYIPQSYAGADDVVDSSKSFVMENFSSYHGTKPGYVDS

SEQ ID NO 40: Amino acid sequence of the CcmH signal sequence and the first 30 amino acids of CRM197

MRFLLGVLMLMISGSALAGADDVVDSSKSFVMENFSSYHGTKPGYVDS

Figure 9G

SEQ ID NO 41: Amino acid sequence of the YraI signal sequence and the first 30 amino acids of CRM197
MSKRTFAVILTLLCSFCIGQALAGADDVVDSSKSFVMENFSSYHGTKPGYVDS

SEQ ID NO 42: Amino acid sequence of the TolB signal sequence and the first 30 amino acids of CRM197
MMKQALRVAFGFLILWASVLHAGADDVVDSSKSFVMENFSSYHGTKPGYVDS

SEQ ID NO 43: Amino acid sequence of the NikA signal sequence and the first 30 amino acids of CRM197
MLSTLRRTLFALLACASFIVHAGADDVVDSSKSFVMENFSSYHGTKPGYVDS

SEQ ID NO 44: Amino acid sequence of the FlgI signal sequence and the first 30 amino acids of CRM197
MIKFLSALILLLVTTAAQAGADDVVDSSKSFVMENFSSYHGTKPGYVDS

SEQ ID NO 45: Amino acid sequence of the DsbA signal sequence and the first 30 amino acids of CRM197
MKKIWLALAGLVLAFSASAGADDVVDSSKSFVMENFSSYHGTKPGYVDS

EXPRESSION SYSTEM

This application is filed pursuant to 35 U.S.C. §371 as a United States National Phase Application of International Patent Application Serial No. PCT/EP2010/065047 filed Oct. 7, 2010, which claims priority to United Kingdom Patent Application No. GB0917647.0 filed Oct. 8, 2009, the contents of which are hereby incorporated by reference.

The present invention relates to the field of the expression of bacterial toxins, in particular diphtheria toxins (including mutant forms of diphtheria toxin, such as CRM197) and includes processes suitable for the expression and manufacture of bulk cultures of such toxins. The invention also provides novel polynucleotides and polypeptides which can be used or produced during the processes of the invention.

Diphtheria toxin is a protein exotoxin produced by the bacterium *Corynebacterium diphtheria*. It is produced as a single polypeptide containing a signal sequence (the tox signal sequence) that is removed by the bacterium on secretion of the protein.

The diphtheria toxin is readily spliced to form two subunits linked by a disulphide bond, Fragment A and Fragment B, as a result of cleavage at residue 190, 192 or 193 (Moskaug et al Biol. Chem. 264: 15709-15713, 1989). Fragment A is the catalytically active portion and is an NAD-dependent ADP-ribosyltransferase which specifically targets a protein synthesis factor EF-2, thereby inactivating EF-2 and shutting down protein synthesis in a cell.

Immunity to a bacterial toxin such as diphtheria toxin may be acquired naturally during the course of infection, or artificially by injection of a detoxified form of the toxin (toxoid) (Germanier, Bacterial Vaccines, Academic Press, Orlando, Fla., 1984). Toxoids have traditionally been made by chemical modification of native toxins (Lingood et al Brit. J. Exp. Path. 44; 177, 1963), rendering them non-toxic while retaining an antigenicity that protects the vaccinated animal against subsequent challenge by the natural toxin. Alternatively, several mutated diphtheria toxins have been described which have reduced toxicity (U.S. Pat. No. 4,709,017, U.S. Pat. No. 4,950,740).

CRM197 is a non-toxic form of the diphtheria toxin but is immunologically indistinguishable from the diphtheria toxin. CRM197 is produced by *C. diphtheriae* infected by the non-toxigenic phage β 197tox-created by nitrosoguanidine mutagenesis of the toxigenic carynephage b (Uchida et al Nature New Biology (1971) 233; 8-11). The CRM197 protein has the same molecular weight as the diphtheria toxin but differs from it by a single base change in the structural gene. This leads to a glycine to glutamine change of amino acid at position 52 which makes fragment A unable to bind NAD and therefore non-toxic (Pappenheimer 1977, Ann Rev, Biochem. 46; 69-94, Rappuoli Applied and Environmental Microbiology September 1983 p 560-564).

Diphtheria toxoid and a mutant form with reduced toxicity, CRM197, are components in many vaccines providing immunity against *Corynebacterium diphtheriae*. Several combination vaccines are known which can prevent *Bordetella pertussis, Clostridium tetani, Corynebacterium diphtheriae*, and optionally Hepatitis B virus and/or *Haemophilus influenzae* type b (see, for instance, WO 93/24148 and WO 97/00697, WO 02/055105).

Diphtheria toxin and mutant forms including CRM197 have also been used in vaccines as safe and effective T-cell dependent carriers for saccharides. CRM197 is currently used in the *Haemophilus influenzae* type b oligosaccharide CRM197 conjugate vaccine (HibTitre®; Lederle Praxis Biologicals, Rochester, N.Y.).

Methods of preparing diphtheria toxoid (DT) are well known in the art. For instance, DT may be produced by purification of the toxin from a culture of *Corynebacterium diphtheriae* followed by chemical detoxification, or may be made by purification of a recombinant, or genetically detoxified analogue of the toxin (for example, CRM197, or other mutants as described in U.S. Pat. No. 4,709,017, U.S. Pat. No. 5,843,711, U.S. Pat. No. 5,601,827, and U.S. Pat. No. 5,917,017).

Production of significant quantities of diphtheria toxins such as CRM197 for use in vaccines has been hindered due to low protein abundance. This problem has been addressed previously by expressing CRM197 in *E. coli* (Bishai et al J Bacteriol. 169:5140-5151), Bishai et al describes the expression of a recombinant fusion protein containing diphtheria toxin (including the tox signal sequence) this led to the production of degraded protein.

Cloning of Diptheria fragments containing the tox signal sequence and expression of these sequences in *Escherichia coli* involves certain difficulties. The expressed protein is secreted into the periplasmic space and this secretion is associated with decreased viability of the host cells (O'Keefe et al Proc. Natl. Acad. Sci. 86:343-346) and increased proteolysis of the recombinant protein (Bishai et al J Bacteriol. 169: 5140-5151). For these reasons removal of the tox signal sequence so that expression is no longer periplasmic has been suggested, this can increase expression of Diphtheria toxoids (Bishai et al).

Accordingly, the present application provides an improved process for making a bacterial toxin by periplasmic expression comprising the steps of a) growing a culture of the bacterial host cell containing an expression vector in which particular signal sequences are linked to the sequence of a bacterial toxin and b) inducing expression of the polypeptide containing particular signal sequences linked to a bacterial toxin such that a bacterial toxin is expressed periplasmically. The present application also provides polynucleotides which are used in the process of the invention.

Production of bacterial toxins in the periplasm may have one or more advantages over cytoplasmic production.
(1) The protein is produced in its mature form after cleavage of the signal peptide, and/or;
(2) The periplasm of *E. coli* is an oxidizing environment that allows the formation of disulphide bonds, this may help produce soluble, correctly folded proteins, and/or;
(3) The periplasm of *E. coli* contains fewer proteases than the cytoplasm, this may help avoid proteolytic cleavage of the expressed protein, and/or;
(4) The periplasm also contains fewer proteins, this allows purer recombinant protein to be obtained.

SUMMARY OF THE INVENTION

In a first aspect of the invention there is provided a polynucleotide comprising a 5' signal sequence portion and a 3' toxin portion wherein;
(a) The 5' signal sequence portion encodes a heterologous polypeptide having an amino acid sequence capable of directing transport of a heterologous protein to the bacterial periplasm; and
(b) the 3' toxin portion encodes a polypeptide having an amino acid sequence at least 90% identical to SEQ ID NO: 32 or fragments thereof encoding at least 15 amino acids and/or at least one B or T cell epitope.

In a second aspect of the invention there is provided a polynucleotide comprising a 5' signal sequence portion and a 3' toxin portion wherein
(a) the 5' signal sequence portion encodes a polypeptide having an amino acid sequence capable of directing transport of a heterologous protein to the bacterial periplasm and wherein the 5' signal sequence is not derived from *C. diphtheriae*; and (b) the 3' toxin portion encodes a polypeptide having an amino acid sequence at least 90% identical to SEQ ID NO: 32 or fragments thereof encoding at least 15 amino acids and/or at least one B or T cell epitope.

In a third aspect of the invention there is provided a polynucleotide comprising a 5' signal sequence portion and a 3' toxin portion wherein the 5' signal portion sequence encodes a signal peptide having an amino acid sequence of (a) SEQ ID NO: 2, 4, 6, 8, 10, 12, 14, 16, 18, 20, 22, 24, or 26;
(b) variants of SEQ ID NO: 2, 4, 6, 8, 10, 12, 14, 16, 18, 20, 22, 24, or 26, varying from the corresponding sequences by 1, 2 or 3 point mutations, amino acid insertions or amino acid deletions, which are capable of directing an expressed protein to the periplasm; or
(c) fragments of at least 10 amino acids of SEQ ID NO: 2, 4, 6, 8, 10, 12, 14, 16, 18, 20, 22, 24, or 26 which are capable of directing an expressed protein to the periplasm;

and the 3' toxin portion encodes a bacterial toxin or fragment or variant thereof.

In a fourth aspect of the invention there is provided a vector comprising the polynucleotide of the invention linked to an inducible promoter.

In a fifth aspect of the invention there is provided a host cell comprising the polynucleotide or the vector of the invention.

In a sixth aspect of the invention there is provided a polypeptide encoded by the polynucleotide of the invention.

In a seventh aspect of the invention there is provided a process for making a bacterial toxin comprising the steps of a) growing a culture of the bacterial host cell of the invention and b) inducing expression of the polypeptide such that a bacterial toxoid is expressed periplasmically.

In an eighth aspect of the invention there is provided a process for making a conjugate comprising the steps of a) making a bacterial toxin using the process of the invention and b) conjugating the bacterial toxin of step a) to an antigen.

In a ninth aspect of the invention there is provided a process for manufacturing a vaccine comprising the steps of a) making a bacterial toxin or conjugate using the process of the invention and b) mixing the bacterial toxin or conjugate thereof with a pharmaceutically acceptable excipient.

TABLE 1

| Lane Number | Signal sequence | Culture temperature | SEQ ID NO nucleotide | SEQ ID NO Amino acid |
|---|---|---|---|---|
| 1 | DsbA | Overnight 23° C. | 25 | 26 |
| 2 | OmpA | Overnight 23° C. | 5 | 6 |
| 3 | NspA | Overnight 23° C. | 7 | 8 |
| 4 | FlgI | Overnight 23° C. | 23 | 24 |
| 5 | TolB | Overnight 23° C. | 19 | 20 |
| 6 | SfmC | Overnight 23° C. | 11 | 12 |
| 7 | TorT | Overnight 23° C. | 9 | 10 |
| 8 | FocC | Overnight 23° C. | 13 | 14 |
| 9 | Ccmh | Overnight 23° C. | 15 | 16 |
| 10 | Yra1 | Overnight 23° C. | 17 | 18 |
| 11 | NikA | Overnight 23° C. | 21 | 22 |
| 12 | PhtE | Overnight 23° C. | 1 | 2 |
| 13 | SipA | Overnight 23° C. | 3 | 4 |
| 14 | Marker | 250, 150, 100 75, 50, 37, 25, 20 | | |
| 15 | DsbA | Non induced | 25 | 26 |
| 16 | DsbA | Overnight 30° C. | 25 | 26 |
| 17 | FocC | Overnight 30° C. | 13 | 14 |
| 18 | CcmH | Overnight 30° C. | 15 | 16 |

Figure 6:
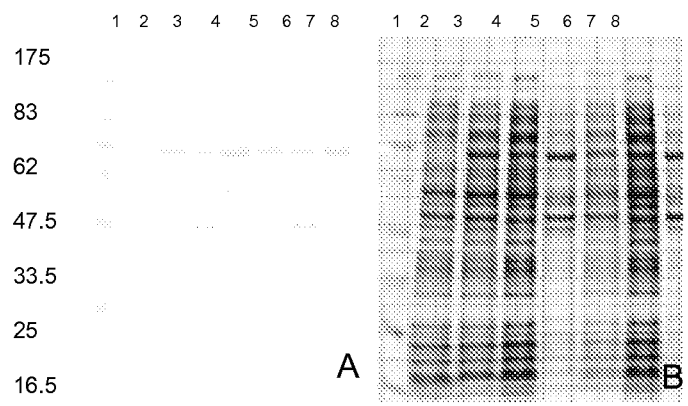

FIG. 6—Gels demonstrating induction of DsbA-CRM197 for 3 hours at 30° C. in three different strains. Novex TG 10-20% gel was used. Panel A is a Western blot stained using anti-DTPa and anti-mouse NBT-BCIP. Panel B is stained using Coomassie blue. Lane 1 contains the molecular weight marker, Lane 2 contains the BLR(DE3) strain which has not been induced, lane 3 contains the BLR(DE3) strain which has been induced, lane 4 contains the soluble fraction from a BLR(DE3) strain that has been induced, lane 5 contains the insoluble fraction from a BLR(DE3) strain that has been induced, lane 6 contains the B834(DE3) strain which has not been induced, lane 7 contains the B834(DE3) induced soluble fraction and lane 8 contains the B834(DE3) induced insoluble fraction.

FIG. 7—Gels comparing the expression of the optimised FIgI construct with or without the addition of 1M potassium phosphate buffer to a concentration of 100 mM in the induction phase. Novex TG 10-20% gel was used. Lane 1 contains the molecular weight marker, lane 2 contains the cell extract at 0 minutes from induction (induction at 30° C.), lane 3 contains cell extract at 2 hours from induction (induction at 30° C.), lane 4 contains cell extract at 4 hours from induction (induction at 30° C.), lane 5 contains cell extract after overnight induction at 30° C., lane 6 contains the medium after 4 hours after induction at 30° C., lane 7 contains the medium over after induction at 30° C. overnight, lane 8 contains cell extract at two hours from induction (induction at 23° C.), lane 9 contains cell extract at 4 hours from induction (induction at 23° C.), lane 10 contains cell extract after overnight induction, lane 11 contains medium 4 hours from induction (induction at 23° C.) and lane 12 contains medium after overnight induction (induction at 23° C.).

Figure 8:
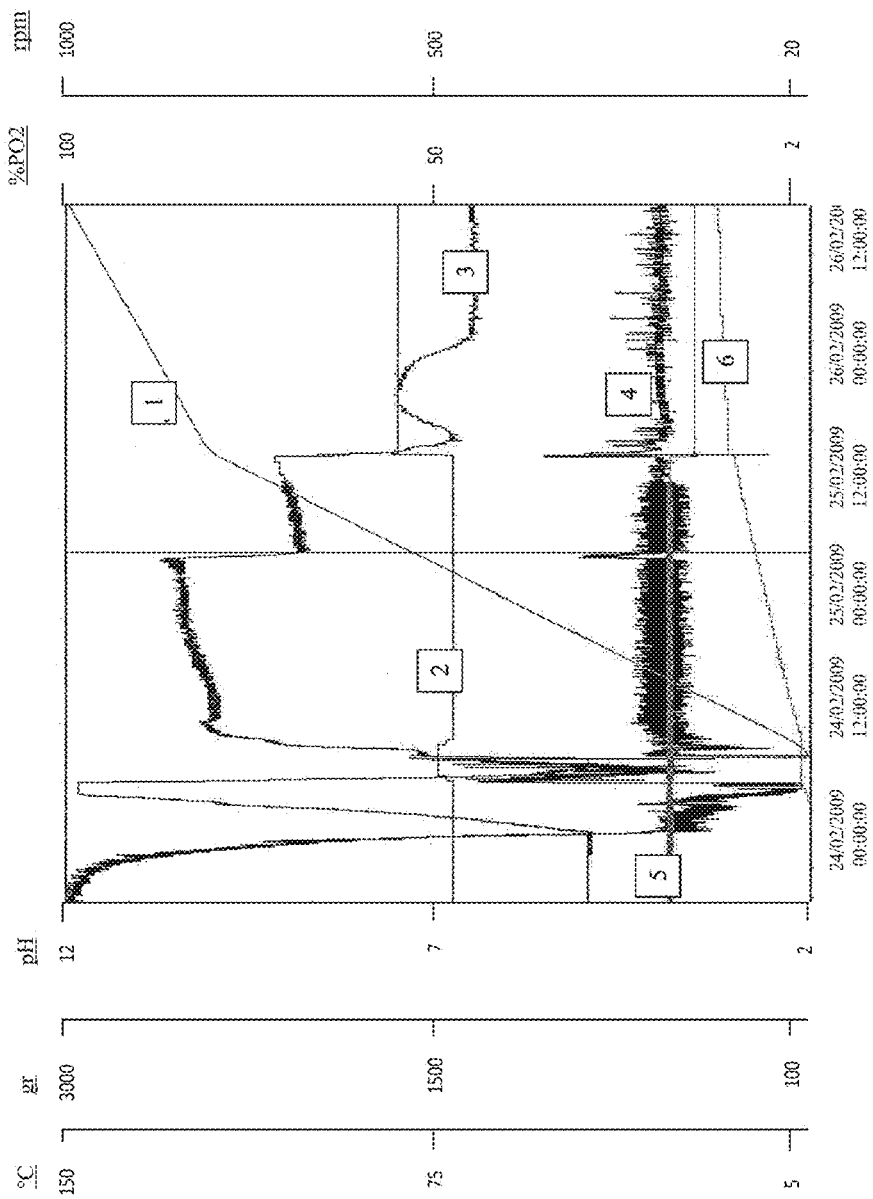

FIG. 8—Depiction of a fermentation profile with the process parameters monitored during 20 liter scale fed-batch fermentation. Line 1 describes the amount of substrate added (grams), line 2 describes the pH, line 3 describes the stirring rate (rpm), line 4 describes the $pO_2$ (%), line 5 describes the temperature (° C.) and line 6 describes the amount of base added (grams).

FIG. 9—Sequence listings of polypeptides and polynucleotides of the invention.

Figure 10:
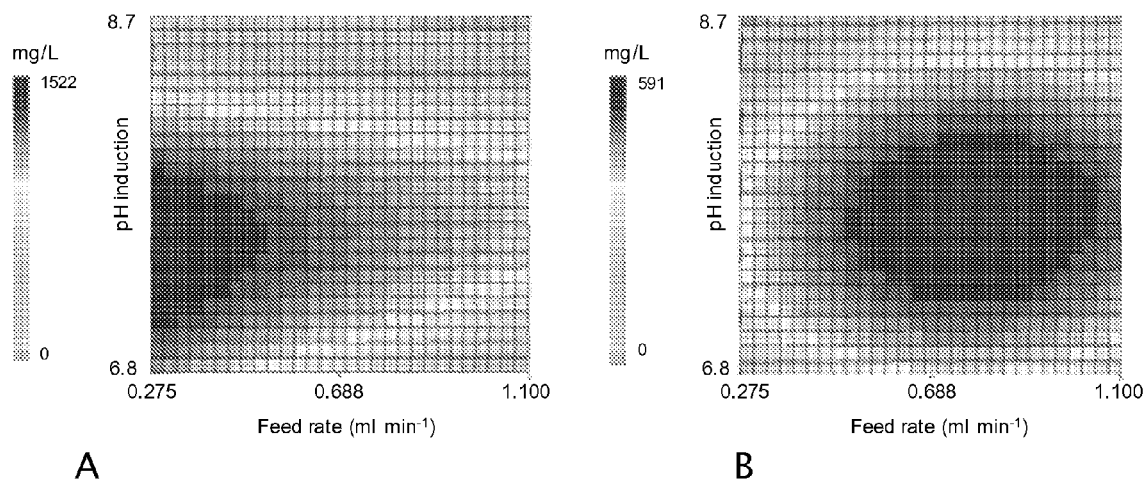

FIG. 10—Depiction of the production of CRM197 in the periplasmic and cell-associated fractions as a function of the feed rate and pH during induction, for growth performed at pH 6.8. The left panel shows periplasmic CRM197 production. The right panel describes cell-associated CRM197 production.

DETAILED DESCRIPTION OF THE INVENTION

Definitions

The term "Polynucleotide(s)" generally refers to any polyribonucleotide or polydeoxyribonucleotide, which may be unmodified RNA or DNA or modified RNA or DNA including single and double-stranded regions/forms.

The term polypeptide refers to any peptide comprising at least ten amino acids.

The term "polynucleotide encoding a peptide" as used herein encompasses polynucleotides that include a sequence encoding a peptide or polypeptide of the invention. The term also encompasses polynucleotides that include a single continuous region or discontinuous regions encoding the peptide or polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

Polynucleotide "variants of the 5' signal sequence portion" are polynucleotide sequences encoding signal sequences which contain, 1, 2, 3, 4 or 5 amino acid substitution, amino acid addition or amino acid deletion mutations compared to the corresponding wild type signal sequence.

An "amino acid deletion" is the removal of one amino acid from the amino acid sequence of a protein.

An "amino acid addition" is the addition of one amino acid from the amino acid sequence of a protein.

An "amino acid substitution is the replacement of one amino acid with another amino acid, in the sequence of a protein.

Polynucleotide "variants of the 3' toxin portion" are polynucleotide sequences which encode polypeptide sequences having 80%, 85%, 90%, 95%, 98% or 100% identity to a toxin polypeptide. A definition for identity is given below.

In general "variants" are optionally polypeptides that vary from the referents by conservative amino acid substitutions, whereby a residue is substituted by another with like characteristics. Typically such substitutions are among Ala, Val, Leu and Ile; among Ser and Thr; among the acidic residues Asp and Glu; among Asn and Gln; and among the basic residues Lys and Arg; or aromatic residues Phe and Tyr.

"Fragments of the 5' signal sequence portion" are sequences which encode at least 10, 15 or 20 amino acids of a signal peptide.

"Fragments of the 3' toxin portion" are sequences which encode a contiguous portion of at least 5, 10, 15, 20, 30, 40, 50, 100 or 200 amino acids of a toxin polypeptide, which optionally have immunogenic activity. A peptide with "immunogenic activity" or which is "immunogenic" is capable (if necessary when coupled to a carrier) of raising an immune response which recognises the respective toxin. Preferred fragments are those polynucleotides which encode a B-cell or T-cell epitope, and recombinant, polynucleotides comprising said polynucleotide fragments. Optionally fragments of these toxins are fragments which are immunogenic.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Methods to determine identity are designed to give the largest match between the sequences tested. Moreover, methods to determine identity are codified in publicly available computer programs. Computer program methods to determine identity between two sequences include, but are not limited to, the GAP program in the GCG program package (Devereux, J., et al., Nucleic Acids Research 12(1): 387 (1984)), BLASTP, BLASTN (Altschul, S. F. et al., J. Molec. Biol. 215: 403-410 (1990), and FASTA (Pearson and Lipman Proc. Natl. Acad. Sci. USA 85; 2444-2448 (1988). The BLAST family of programs is publicly available from NCBI and other sources (BLAST Manual, Altschul, S., et al., NCBI NLM NIH Bethesda, MD 20894; Altschul, S., et al., J. Mol. Biol. 215: 403-410 (1990). The well known Smith Waterman algorithm may also be used to determine identity.

Parameters for polypeptide sequence comparison include the following:

Algorithm: Needleman and Wunsch, J. Mol Biol. 48: 443-453 (1970)

Comparison matrix: BLOSSUM62 from Henikoff and Henikoff,

Proc. Natl. Acad. Sci. USA. 89:10915-10919 (1992)

Gap Penalty: 8

Gap Length Penalty: 2

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:

Algorithm: Needleman and Wunsch, J. Mol Biol. 48: 443-453 (1970)

Comparison matrix: matches=+10, mismatch=0

Gap Penalty: 50
Gap Length Penalty: 3
Available as: The "gap" program from Genetics Computer Group, Madison Wis. These are the default parameters for nucleic acid comparisons.

The term 'signal peptide' or 'signal polypeptide' refers to a peptide which is capable of directing an expressed protein to the periplasm.

The term "bacterial toxin" encompasses both toxins and toxoids.

The term "toxoid" describes toxins which have been partially or completely inactivated by, for example the introduction of point mutations, deletions or insertions.

The terms "comprising", "comprise" and "comprises" herein is intended by the inventors to be optionally substitutable with the terms "consisting of", "consist of", and "consists of", respectively, in every instance.

The term 'heterologous protein refers to a protein which is not native to the cell type in which it is expressed. Similarly the term 'heterologous polypeptide' refers to a polypeptide which is not native to the cell type in which it is expressed.

The term 'polypeptide not derived from *C. diphtheriae*' refers to a polypeptide which is different in sequence to a polypeptide found in native (not recombinant) *C. diphtheriae*.

Polynucleotides of the Invention

One aspect of the invention relates to polynucleotides encoding toxins which are periplasmically expressed.

In general the presence of a signal sequence on the protein facilitates the transport of the protein into the periplasm (prokaryotic hosts) or the secretion of the protein (eukaryotic hosts). In prokaryotic hosts the signal sequence directs the nascent protein across the inner membrane into the periplasmic space; the signal sequence is then cleaved. A signal sequence is capable of directing an expressed protein to the periplasm if, when it is attached to a polypeptide of interest, during translation of the polypeptide in a gram negative bacteria, more of said polypeptide is found in the periplasm of a gram negative bacteria than in the absence of the signal sequence. In an embodiment at least 50, 60, 70, 80, 90 or 100% of the polypeptide of interest is directed to the periplasm when expressed in a gram negative bacterium such as *E. coli*.

An assay to test whether a signal sequence is capable of directing periplasmic expression can be carried out using reporter proteins. For example a periplasmic signal sequence can be spliced upstream of a gene for a green fluorescent protein, this protein can be expressed in a host cell of the invention. A microscope can be used to judge the comparative levels of the green fluorescent protein in the cytoplasm and the periplasm.

A protein or peptide is transported co-translationally if transport occurs before the synthesis of a substantial amount of the polypeptide chain. SEQ ID NO: 2, 4, 10, 12, 14, 16, 18, 20, 22, 24, or 26 encode peptides which are capable of directing an expressed protein to the periplasm through co-translational transport, whereas SEQ ID NOs: 6 and 8 encode peptides which are capable of directing an expressed protein to the periplasm through post-translational transport.

In an embodiment there is provided a polynucleotide (for example for expression of a toxin in a bacterial cell) comprising a 5' signal sequence portion and a 3' toxin portion, wherein
 (a) The 5' signal sequence portion encodes a heterologous (signal) polypeptide having an amino acid sequence capable of directing transport of a heterologous (toxin) protein to the bacterial periplasm; and
 (b) the 3' toxin portion encodes a polypeptide having an amino acid sequence at least 75%, 80%, 85%, 90%, 95% or 99% identical to SEQ ID NO: 32 or fragments thereof (which may be immunogenic) encoding at least 15 (contiguous) amino acids and/or at least one B or T cell epitope.

In a further embodiment there is provided a polynucleotide (for expression of a polypeptide in a bacterial cell) comprising a 5' signal sequence portion and a 3' toxin portion, wherein
 (a) The 5' signal sequence portion encodes a polypeptide having an amino acid sequence capable of directing transport of a heterologous protein to the bacterial periplasm and wherein the 5' signal sequence portion is not derived from *C. diphtheriae*; and
 (b) the 3' toxin portion encodes a polypeptide having an amino acid sequence at least 90% identical to SEQ ID NO: 32 or fragments thereof encoding at least 15 amino acids and/or at least one B or T cell epitope.

In one embodiment the 5' signal sequence is not the tox signal sequence from *Corynebacterium diphtheriae*.

Figure 4:
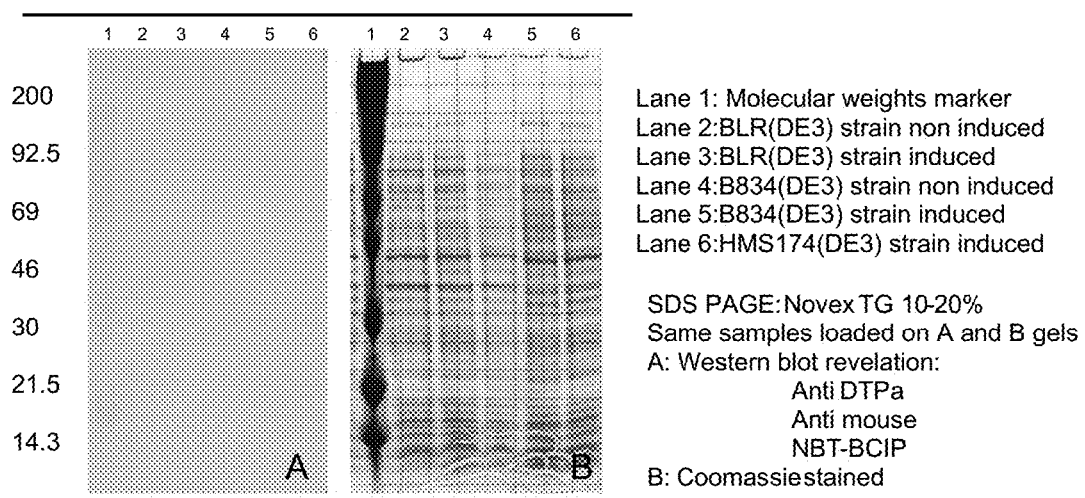
FIG. 4—Gels demonstrating induction of DsbA-CRM197 3 hours after treatment with IPTG at 30° C. in three different strains. Novex TG 10-20% gel was used. Panel A gel is a Western blot stained using anti-DTPa and anti-mouse NBT-BCIP. Panel B gel is stained using Coomassie blue. Lane 1 contains the molecular weight marker, lane 2 contains a BLR (DE3) strain which has not been induced, lane 3 contains a BLR(DE3) strain which has been induced, lane 4 contains a B834 (DE3) strain which has not been induced, lane 5 contains a B384 (DE3) strain which has been induced and lane 6 contains an HMS174(DE3) strain which has been induced.
Figure 5:
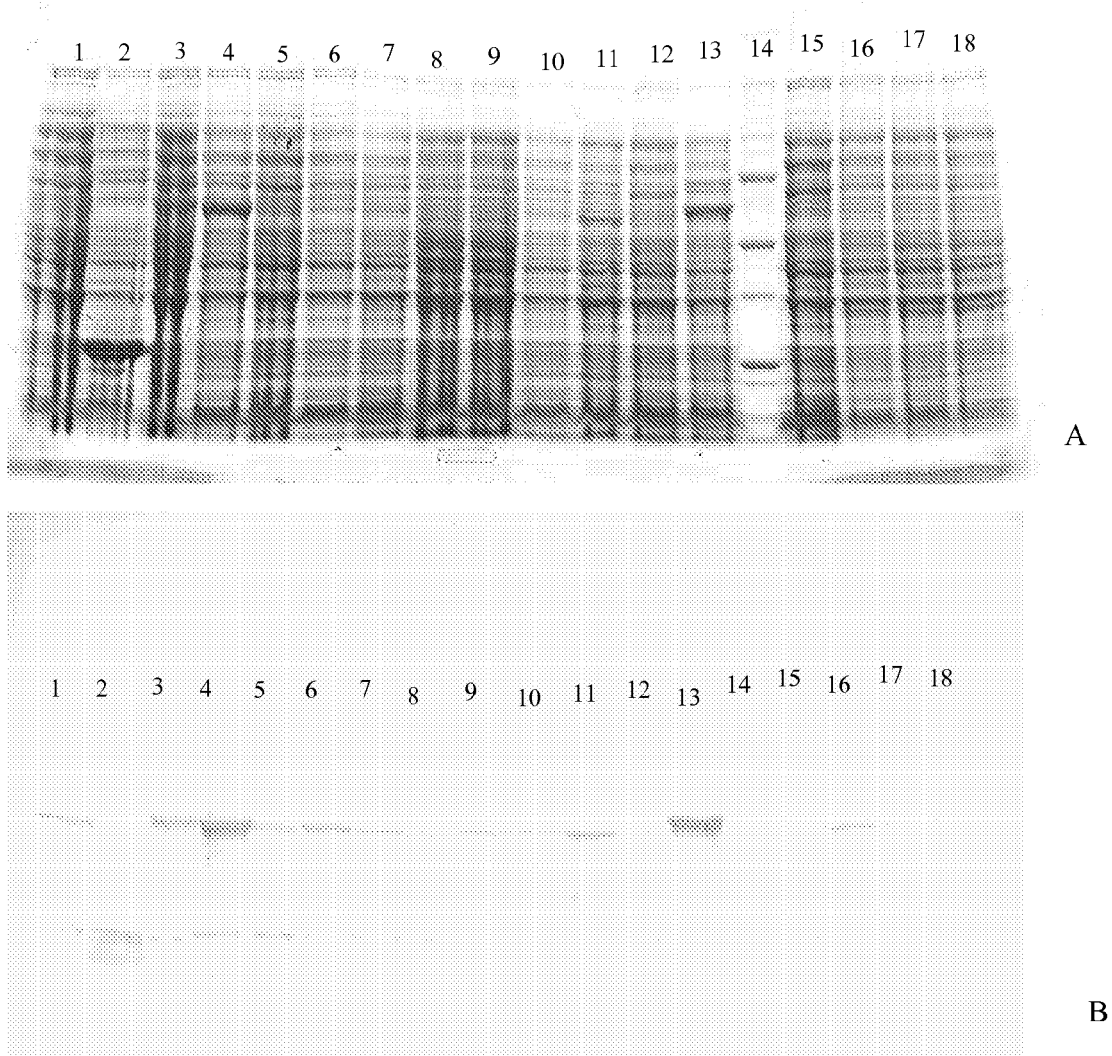
FIG. 5—Gels demonstrating expression of CRM-197 in the bacterial cell and in the culture medium. Panel B gel shows a Western blot, stained using anti-DTPa and anti-mouse NBT-BCIP. Panel A is stained using Coomassie blue. The contents of each lane are described in the table below.

It is within the capabilities of the skilled person to identify B and T cell epitopes. B cell epitopes may be identified by 2D structure prediction, for example using the PSIPRED program (from David Jones, Brunel Bioinformatics Group, Dept. Biological Sciences, Brunel University, Uxbridge UB8 3PH, UK) (FIG. 4). The antigenic index is calculated on the basis of the method described by Jameson and Wolf (CABIOS 4:181-186 [1988]). The parameters used in this program are the antigenic index and the minimal length for an antigenic peptide. An antigenic index of 0.9 for a minimum of 5 consecutive amino acids was used as threshold in the program. T cell epitopes may be identified, for example, by the tepitope method describe by Sturniolo at al. (Nature Biotech. 17: 555-561 [1999]).

For clarity the phrase 'having an amino acid sequence capable of directing transport of a heterologous protein to the bacterial periplasm' means the same as 'having an amino acid sequence capable of directing transport to the bacterial periplasm of a heterologous protein'.

In a further embodiment this polynucleotide may encode a polypeptide having an amino acid sequence capable of directing co-translational transport of a heterologous protein to the bacterial periplasm.

Optionally the 3' toxin portion encodes SEQ ID NO 32. Optionally the 3' toxin portion encodes DT. Optionally the 3' toxin portion comprises SEQ ID NO: 31.

Optionally the 5' signal sequence portion encodes any one of SEQ ID NO: 2, 4, 6, 8, 10, 12, 14, 16, 18, 20, 22, 24, or 26, or any one of SEQ ID NO: 2, 4, 10, 12, 14, 16, 18, 20, 22, 24, or 26, or any one of SEQ ID NO: 2, 4, 10, 12, 14, 16, 18, 20, 22, or 24, or SEQ ID NO: 24 or any one of SEQ ID NO: 2, 4, or 24, or any one of SEQ ID NO: 2, 10, or 24, or any one of SEQ ID NO: 2, 12, or 24, or any one of SEQ ID NO: 2, 14, or 24, or any one of SEQ ID NO: 4, 10 or 24, or any one of SEQ ID NO: 4, 12, or 24, or any one of SEQ ID NO: 4, 16, or 24, or any one of SEQ ID NO: 4, 18 or 24, or any one of SEQ ID NO: 4, 20 or 24, or any one of SEQ ID NO: 4, 22, or 24, or any one of SEQ ID NO: 10, 12, or 24, or any one of SEQ ID NO: 10, 14, or 24, or any one of SEQ ID NO: 10, 16, or 24, or any one of SEQ ID NO: 10, 18, or 24, or any one of SEQ ID NO: 10, 22 or 24, or any one of SEQ ID NO: 12, 14, or 24, or any one of SEQ ID NO: 12, 16, or 24, or any one of SEQ ID NO: 12, 18, or 24, or any one of SEQ ID NO: 12, 20, or 24, or any one of SEQ ID NO: 12, 22, or 24, or any one of SEQ ID NO: 14, 16, or 24, or any one of SEQ ID NO: 14, 18, or 24, or any one of SEQ ID NO: 14, 20 or 24, or any one of SEQ ID NO: 14, 22, or 24, or any one of SEQ ID NO: 16, 18, or 24, or any one of SEQ ID NO: 16, 20 or 24, or any one of SEQ ID NO:

16, 22, or 24, or any one of SEQ ID NO: 18, 20 or 24, or any one of SEQ ID NO 18, 22, or 24.

In a further embodiment the 5' signal sequence portion encodes (variants containing) 1, 2 or 3 point mutations, insertions or deletions, of any one of SEQ ID NO: 2, 4, 6, 8, 10, 12, 14, 16, 18, 20, 22, 24, or 26 or any one of SEQ ID NO: 2, 4, 10, 12, 14, 16, 18, 20, 22, 24, or 26, or any one of SEQ ID NO: 2, 4, 10, 12, 14, 16, 18, 20, 22, or 24, or SEQ ID NO: 24 or any one of SEQ ID NO: 2, 4, or 24, or any one of SEQ ID NO: 2, 10, or 24, or any one of SEQ ID NO: 2, 12, or 24, or any one of SEQ ID NO: 2, 14, or 24, or any one of SEQ ID NO: 4, 10 or 24, or any one of SEQ ID NO: 4, 12, or 24, or any one of SEQ ID NO: 4, 16, or 24, or any one of SEQ ID NO: 4, 18 or 24, or any one of SEQ ID NO: 4, 20 or 24, or any one of SEQ ID NO: 4, 22, or 24, or any one of SEQ ID NO: 10, 12, or 24, or any one of SEQ ID NO: 10, 14, or 24, or any one of SEQ ID NO: 10, 16, or 24, or any one of SEQ ID NO: 10, 18, or 24, or any one of SEQ ID NO: 10, 22 or 24, or any one of SEQ ID NO: 12, 14, or 24, or any one of SEQ ID NO: 12, 16, or 24, or any one of SEQ ID NO: 12, 18, or 24, or any one of SEQ ID NO: 12, 20, or 24, or any one of SEQ ID NO: 12, 22, or 24, or any one of SEQ ID NO: 14, 16, or 24, or any one of SEQ ID NO: 14, 18, or 24, or any one of SEQ ID NO: 14, 20 or 24, or any one of SEQ ID NO: 14, 22, or 24, or any one of SEQ ID NO: 16, 18, or 24, or any one of SEQ ID NO: 16, 20 or 24, or any one of SEQ ID NO: 16, 22, or 24, or any one of SEQ ID NO: 18, 20 or 24, or any one of SEQ ID NO 18, 22, or 24.

In a further embodiment the 5' signal sequence portion encodes fragments of at least 10, 12, 15, 18 or 20 amino acids of any one of SEQ ID NO: 2, 4, 6, 8, 10, 12, 14, 16, 18, 20, 22, 24, or 26 or any one of SEQ ID NO: 2, 4, 10, 12, 14, 16, 18, 20, 22, 24, or 26, or any one of SEQ ID NO: 2, 4, 10, 12, 14, 16, 18, 20, 22, or 24, or SEQ ID NO: 24, or any one of SEQ ID NO: 2, 4, or 24, or any one of SEQ ID NO: 2, 10, or 24, or any one of SEQ ID NO: 2, 12, or 24, or any one of SEQ ID NO: 2, 14, or 24, or any one of SEQ ID NO: 4, 10 or 24, or any one of SEQ ID NO: 4, 12, or 24, or any one of SEQ ID NO: 4, 16, or 24, or any one of SEQ ID NO: 4, 18 or 24, or any one of SEQ ID NO: 4, 20 or 24, or any one of SEQ ID NO: 4, 22, or 24, or any one of SEQ ID NO: 10, 12, or 24, or any one of SEQ ID NO: 10, 14, or 24, or any one of SEQ ID NO: 10, 16, or 24, or any one of SEQ ID NO: 10, 18, or 24, or any one of SEQ ID NO: 10, 22 or 24, or any one of SEQ ID NO: 12, 14, or 24, or any one of SEQ ID NO: 12, 16, or 24, or any one of SEQ ID NO: 12, 18, or 24, or any one of SEQ ID NO: 12, 20, or 24, or any one of SEQ ID NO: 12, 22, or 24, or any one of SEQ ID NO: 14, 16, or 24, or any one of SEQ ID NO: 14, 18, or 24, or any one of SEQ ID NO: 14, 20 or 24, or any one of SEQ ID NO: 14, 22, or 24, or any one of SEQ ID NO: 16, 18, or 24, or any one of SEQ ID NO: 16, 20 or 24, or any one of SEQ ID NO: 16, 22, or 24, or any one of SEQ ID NO: 18, 20 or 24, or any one of SEQ ID NO 18, 22, or 24 which are capable of directing transport of a protein to the bacterial periplasm.

In a further aspect of the invention there is provided a polynucleotide comprising a 5' signal sequence portion and a 3' toxin portion, wherein the 5' signal portion sequence encodes a signal peptide having an amino acid sequence of;
(a) SEQ ID NO: 2, 4, 6, 8, 10, 12, 14, 16, 18, 20, 22, 24, or 26; or SEQ ID NO: 2, 4, 10 12, 14, 16, 18, 20, 22, 24, or 26; or SEQ ID NO: NO: 2, 4, 10, 12, 14, 16, 18, 20, 22, or 24; or SEQ ID NO: 24, or SEQ ID NO: 2, 4, or 24; or SEQ ID NO: 2, 10, or 24; or SEQ ID NO: 2, 12, or 24; or SEQ ID NO: 2, 14, or 24; or SEQ ID NO: 4, 10 or 24; or SEQ ID NO: 4, 12, or 24; or SEQ ID NO: 4, 16, or 24; or SEQ ID NO: 4, 18 or 24; or SEQ ID NO: 4, 20 or 24; or SEQ ID NO: 4, 22, or 24; or SEQ ID NO: 10, 12, or 24; or SEQ ID NO: 10, 14, or 24; or SEQ ID NO: 10, 16, or 24; or SEQ ID NO: 10, 18, or 24; or SEQ ID NO: 10, 22 or 24; or SEQ ID NO: 12, 14, or 24; or SEQ ID NO: 12, 16, or 24; or SEQ ID NO: 12, 18, or 24; or SEQ ID NO: 12, 20, or 24; or SEQ ID NO: 12, 22, or 24; or SEQ ID NO: 14, 16, or 24; or SEQ ID NO: 14, 18, or 24; or SEQ ID NO: 14, 20 or 24; or SEQ ID NO: 14, 22, or 24; or SEQ ID NO: 16, 18, or 24; or SEQ ID NO: 16, 20 or 24; or SEQ ID NO: 16, 22, or 24; or SEQ ID NO: 18, 20 or 24; or any one of SEQ ID NO 18, 22, or 24.

(b) (variants of) SEQ ID NO: 2, 4, 6, 8, 10, 12, 14, 16, 18, 20, 22, 24, or 26; or SEQ ID NO: 2, 4, 10 12, 14, 16, 18, 20, 22, 24, or 26; or SEQ ID NO: NO: 2, 4, 10, 12, 14, 16, 18, 20, 22, or 24; or SEQ ID NO: 24, or SEQ ID NO: 2, 4, or 24; or SEQ ID NO: 2, 10, or 24; or SEQ ID NO: 2, 12, or 24; or SEQ ID NO: 2, 14, or 24; or SEQ ID NO: 4, 10 or 24; or SEQ ID NO: 4, 12, or 24; or SEQ ID NO: 4, 16, or 24; or SEQ ID NO: 4, 18 or 24; or SEQ ID NO: 4, 20 or 24; or SEQ ID NO: 4, 22, or 24; or SEQ ID NO: 10, 12, or 24; or SEQ ID NO: 10, 14, or 24; or SEQ ID NO: 10, 16, or 24; or SEQ ID NO: 10, 18, or 24; or SEQ ID NO: 10, 22 or 24; or SEQ ID NO: 12, 14, or 24; or SEQ ID NO: 12, 16, or 24; or SEQ ID NO: 12, 18, or 24; or SEQ ID NO: 12, 20, or 24; or SEQ ID NO: 12, 22, or 24; or SEQ ID NO: 14, 16, or 24; or SEQ ID NO: 14, 18, or 24; or SEQ ID NO: 14, 20 or 24; or SEQ ID NO: 14, 22, or 24; or SEQ ID NO: 16, 18, or 24; or SEQ ID NO: 16, 20 or 24; or SEQ ID NO: 16, 22, or 24; or SEQ ID NO: 18, 20 or 24; or any one of SEQ ID NO 18, 22, or 24 varying from the corresponding sequences by 1, 2 or 3 point mutations, amino acid insertions or amino acid deletions which are capable of directing an expressed protein to the periplasm; or (c) fragments of at least 10 amino acids of SEQ ID NO: 2, 4, 6, 8, 10, 12, 14, 16, 18, 20, 22, 24, or 26; or SEQ ID NO: 2, 4, 10 12, 14, 16, 18, 20, 22, 24, or 26; or SEQ ID NO: NO: 2, 4, 10, 12, 14, 16, 18, 20, 22, or 24; or SEQ ID NO: 24, or SEQ ID NO: 2, 4, or 24; or SEQ ID NO: 2, 10, or 24; or SEQ ID NO: 2, 12, or 24; or SEQ ID NO: 2, 14, or 24; or SEQ ID NO: 4, 10 or 24; or SEQ ID NO: 4, 12, or 24; or SEQ ID NO: 4, 16, or 24; or SEQ ID NO: 4, 18 or 24; or SEQ ID NO: 4, 20 or 24; or SEQ ID NO: 4, 22, or 24; or SEQ ID NO: 10, 12, or 24; or SEQ ID NO: 10, 14, or 24; or SEQ ID NO: 10, 16, or 24; or SEQ ID NO: 10, 18, or 24; or SEQ ID NO: 10, 22 or 24; or SEQ ID NO: 12, 14, or 24; or SEQ ID NO: 12, 16, or 24; or SEQ ID NO: 12, 18, or 24; or SEQ ID NO: 12, 20, or 24; or SEQ ID NO: 12, 22, or 24; or SEQ ID NO: 14, 16, or 24; or SEQ ID NO: 14, 18, or 24; or SEQ ID NO: 14, 20 or 24; or SEQ ID NO: 14, 22, or 24; or SEQ ID NO: 16, 18, or 24; or SEQ ID NO: 16, 20 or 24; or SEQ ID NO: 16, 22, or 24; or SEQ ID NO: 18, 20 or 24; or any one of SEQ ID NO 18, 22, or 24 which are capable of directing an expressed protein to the periplasm;

and the 3' toxin portion encodes a bacterial toxin or fragment or variant thereof.

There is further provided a polynucleotide comprising a 5' signal sequence portion and a 3' toxin portion, wherein the 5' signal portion sequence encodes a signal peptide having an amino acid sequence of
(d) SEQ ID NO: 2, 4, 6, 8, 10, 12, 14, 16, 18, 20, 22, 24, or 26;
(e) variants of SEQ ID NO: 2, 4, 6, 8, 10, 12, 14, 16, 18, 20, 22, 24, or 26, varying from the corresponding sequences by 1, 2 or 3 point mutations, amino acid insertions or amino acid deletions, which are capable of directing an expressed protein to the periplasm; or (f) fragments of at least 10 amino acids of SEQ ID NO: 2, 4, 6, 8, 10, 12, 14, 16, 18, 20, 22, 24, or 26 which are capable of directing an expressed protein to the periplasm;

and the 3' toxin portion encodes a bacterial toxin or fragment or variant thereof.

In one embodiment the 5' signal sequence portion of the polynucleotide of the invention encodes at least one of SEQ ID NO: 2, 4, 6, 8, 10, 12, 14, 16, 18, 20, 22, 24, or 26. In a further embodiment the 5' signal sequence portion of the polynucleotide of the invention encodes at least one of SEQ ID NO: 2, 4, 10, 12, 14, 16, 18, 20, 22, 24, or 26. In one embodiment the 5' signal sequence portion of the polynucleotide of the invention encodes at least one of SEQ ID NO: 2, 4, 6, 8, 10, 12, 14, 16, 18, 20, 22, 24, or 26; or SEQ ID NO: 2, 4, 10 12, 14, 16, 18, 20, 22, 24, or 26; or SEQ ID NO: NO: 2, 4, 10, 12, 14, 16, 18, 20, 22, or 24; or SEQ ID NO: 24, or SEQ ID NO: 2, 4, or 24; or SEQ ID NO: 2, 10, or 24; or SEQ ID NO: 2, 12, or 24; or SEQ ID NO: 2, 14, or 24; or SEQ ID NO: 4, 10 or 24; or SEQ ID NO: 4, 12, or 24; or SEQ ID NO: 4, 16, or 24; or SEQ ID NO: 4, 18 or 24; or SEQ ID NO: 4, 20 or 24; or SEQ ID NO: 4, 22, or 24; or SEQ ID NO: 10, 12, or 24; or SEQ ID NO: 10, 14, or 24; or SEQ ID NO: 10, 16, or 24; or SEQ ID NO: 10, 18, or 24; or SEQ ID NO: 10, 22 or 24; or SEQ ID NO: 12, 14, or 24; or SEQ ID NO: 12, 16, or 24; or SEQ ID NO: 12, 18, or 24; or SEQ ID NO: 12, 20, or 24; or SEQ ID NO: 12, 22, or 24; or SEQ ID NO: 14, 16, or 24; or SEQ ID NO: 14, 18, or 24; or SEQ ID NO: 14, 20 or 24; or SEQ ID NO: 14, 22, or 24; or SEQ ID NO: 16, 18, or 24; or SEQ ID NO: 16, 20 or 24; or SEQ ID NO: 16, 22, or 24; or SEQ ID NO: 18, 20 or 24; or any one of SEQ ID NO 18, 22, or 24. The nucleotide sequences encoded by SEQ ID NO: 2, 4, 6, 8, 10, 12, 14, 16, 18, 20, 22, 24, or 26 may be identical to the corresponding polynucleotide sequences of SEQ ID NO: 1, 3, 5, 7, 9, 11, 13, 15, 17, 19, 21, 23, or 25. Alternatively it may be any sequence, which as a result of the redundancy (degeneracy) of the genetic code, also encodes polypeptides of SEQ ID NO: 2, 4, 6, 8, 10, 12, 14, 16, 18, 20, 22, 24, or 26. Alternatively the polynucleotide may comprise a portion that encodes SEQ ID NO:33-45.

The polynucleotides of the invention may also comprise a 5' signal sequence portion which encodes a variant of SEQ ID NO: 2, 4, 6, 8, 10, 12, 14, 16, 18, 20, 22, 24, or 26 that is capable of directing a protein to the periplasm.

The present invention also provides for a 5' signal sequence portion comprising a fragment of SEQ ID NO: 2, 4, 6, 8, 10, 12, 14, 16, 18, 20, 22, 24, or 26. Fragments of the invention consist of contiguous portions of at least, 10, 15, or 20 amino acids from SEQ ID NO: 2, 4, 6, 8, 10, 12, 14, 16, 18, 20, 22, 24, or 26. In an embodiment the fragments lead to at least 50, 60, 70, 90, 90 or 100% of the polypeptide encoded toxin being transported to the periplasm. In a further embodiment the fragments have the same or substantially the same periplasmic transport properties as the polypeptide comprising the corresponding amino acid sequence from SEQ ID NO: 2, 4, 6, 8, 10, 12, 14, 16, 18, 20, 22, 24, or 26. In a further embodiment the fragments are capable of directing co-translational transport of a polypeptide to the periplasm.

The 3' toxin portion encodes any bacterial toxin. In one embodiment the encoded bacterial toxin is diphtheria, tetanus, pertussis or pneumolysin toxin.

In one embodiment the 3' toxin portion encodes a bacterial toxoid for example Diphtheria toxoid or CRM 197. Optionally the 3' toxin portion encodes the amino acid sequence described in SEQ ID NO:32. In a further embodiment the 3' toxin portion comprises the nucleotide sequence of SEQ ID NO: 31. In an embodiment the polypeptide encodes SEQ ID NO:33-45.

Alternatively the 3' portion may encode any fragment of at least 10, 15, 25, 35, 50, 100, 150 amino acids or variant with 80%, 85%, 90%, 95%, 98% or 99% sequence homology of the above described toxin or toxoid.

Optionally the 5' signal sequence portion is directly 5' of the 3' toxin portion. Alternatively they are separated by at least 3, 6, 9, 12, 21, 51, 99, 300 or 1000 further nucleotides. For example these nucleotides may encode one or more further peptide sequences of at least 10, 20, 30, 50, 100, 200 or 500 amino acids.

In addition for each and every polynucleotide of the invention there is provided a polynucleotide complementary to it. It is preferred that these complementary polynucleotides are fully complementary to each polynucleotide with which they are complementary.

Also the invention contemplates the expression of any of the polynucleotides within a sequence coding for a larger protein such as a precursor or a fusion protein. It is often advantageous to include an additional amino acid sequence which contains secretory or leader sequences, pro-sequences, sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

In an embodiment the 5' signal sequence portion is not the tox signal sequence of C. diphtheriae.

Polypeptide of the Invention

The present invention also provides for polypeptides encoded by the polynucleotides of the invention. In addition fragments and variants of these polypeptides are provided.

The invention encompasses polypeptides encoding polynucleotides of the invention.

Fragments of these polypeptides are also encompassed by the invention. The fragments contain segments from both the 5' signal sequence portion and 3' toxin portion. In a further embodiment these fragments comprise at least 10, 15 or 20 amino acids of a signal peptide. In an embodiment these fragments comprise at least 10, 15 or 20 of the amino acids from SEQ ID NO: 2, 4, 6, 8, 10, 12, 14, 16, 18, 20, 22, 24, or 26 or SEQ ID NO: 33-45.

In an embodiment these fragments are at least 50%, 60%, 70%, 80%, 90% or 100% directed to the periplasm when expressed in a gram negative bacterium such as E. coli.

The invention also encompasses fusion proteins including the polypeptide or polypeptide fragments of the invention.

The polypeptides, or immunogenic fragments, of the invention may be a part of a larger protein such as a precursor or a fusion protein. It is often advantageous to include an additional amino acid sequence which contains sequences which aid in purification such as multiple histidine residues, or an additional sequence for stability during recombinant production. Furthermore, addition of exogenous polypeptide or lipid tail or polynucleotide sequences to increase the immunogenic potential of the final molecule is also considered.

Vectors and Host Cells

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known to those skilled in the art from genetically engineered host cells comprising expression systems. Accordingly, in a further aspect, the present invention relates to expression systems that comprise a polynucleotide or polynucleotides of the present invention, to host cells which are genetically engineered with such expression systems, and to the production of polypeptides of the invention by recombinant techniques. In a further aspect of the invention the present invention relates to a polynucleotide of the invention linked to an inducible promoter such that when the promoter is induced a polypeptide encoded by the polynucleotide is expresssed. A further aspect of the invention comprises said vector wherein the inducible promoter is activated by addition of a sufficient quantity of IPTG. Optionally this is at a concentration of between 0.1 and 10 mM, 0.1 and 5 mM, 0.1 and 2.5 mM, 0.2 and 10 mM, 0.2 and 5 mM, 0.2 and 2.5 mM, 0.4 and 10 mM, 1 and 10 mM, 1 and 5 mM, 2.5 and 10 mM, 2.5 and 5 mM, 5 and 10 mM.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., BASIC METHODS IN MOLECULAR BIOLOGY, (1986) and Sambrook, et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, conjugation, transduction, scrape loading, ballistic introduction and infection.

Representative examples of appropriate hosts include gram negative bacterial cells, such as cells of, *E. coli, Acinetobacter, Actinobacillus, Bordetella, Brucella, Campylobacter, Cyanobacteria, Enterobacter, Erwinia, Franciscella, Helicobacter, hemophilus, Klebsiella, Legionella, Moraxella, Neisseria, Pasteurella, Proteus, Pseudomonas, Salmonella, Serratia, Shigella, Treponema, Vibrio, Yersinia*. In a further aspect of the invention the host cell is an *Escherichia coli* cell.

A great variety of expression systems can be used to produce the polypeptides of the invention. In one embodiment the vector is derived from bacterial plasmids. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

Fermentation

In a further aspect of the invention there is provided a process for making a bacterial toxin comprising the steps of a) growing a culture of the bacterial host cell of the invention and b) inducing expression of the polypeptide such that a bacterial toxoid is expressed periplasmically.

In a further embodiment of the invention there is provided a process for periplasmic expression of a recombinant polypeptide by
A. Growing a culture of a gram-negative host cell; and
B. Inducing expression of a polypeptide such that a protein is expressed periplasmically;

wherein one or more of the following steps is actioned during expression:
i. The pH of step a) is lower than the pH of step b);
ii. The temperature of step a) is higher than the temperature of step b); or
iii. The substrate feed rate of step a) is higher than the substrate feed rate of step b).

In one embodiment step step i, step ii, step iii, step i and step ii, step i and step iii, step ii and step iii or step i, step ii and step iii are actioned. In a further embodiment a polynucleotide of the invention is expressed.

Polypeptide expression is induced when an inducing agent such as IPTG is added to a culture of host cells, causing expression of polypeptide at an increased rate.

In one embodiment the pH of step a) is the same as the pH of step b), in a second embodiment the pH of step a) is lower than the pH of step b) i.e. the pH of step b) is made higher than that of step a).

The person skilled in the art will recognise how to effect a change between step a) and step b). A change in a condition (e.g. pH, temperature or substrate feed rate) between step a) and step b) means the general average condition during step a) or step b) is as reported and may be assessed for instance, if there has been no other intervention, just prior (e.g. 5 seconds, 15 seconds, 30 seconds, 1 minute, 15 minutes, 30 minutes or one hour) to induction (step a) or just after (e.g. 5 seconds, 15 seconds, 30 seconds, 1 minute, 15 minutes, 30 minutes or one hour) induction (step b). Clearly the inventors also envisage that the intervention to change fermentation conditions may occur slightly before or slightly after induction to achieve the same technical result but in such a scenario again the general or average condition during step a) or step b) will have changed as disclosed herein.

In a further embodiment the pH of step a) ranges from 5.0-7.0, 5.0-6.0, 6.0-7.0 or from 6.5-7.0.

In an embodiment the pH in step b) is maintained. In an embodiment the pH is maintained at greater than pH 6.5, 7.0, 7.5, 8.0, 8.5, 9.0, 9.5, 10.0 or between 6.5 and 10.0, 6.5 and 9.5, 6.5 and 9.0, 6.5 and 8.5, 6.5 and 7.5, 6.5 and 7.0, 7.0 and 10.0, 7.0 and 9.5, 7.0 and 9.0, 7.0 and 8.5, 7.0 and 8.0, 7.0 and 7.5, 7.5 and 10.0, 7.5 and 9.5, 7.5 and 9.0, 7.5 and 8.5, 7.5 and 8.0, 8.0 and 10.0, 8.0 and 9.5, 8.0 and 9.0, 8.0 and 8.5, 8.5 and 10.0, 8.5 and 9.5, 8.0 and 9.0, 8.0 and 8.5, 8.5 and 10.0, 8.5 and 9.5, 8.5 and 9.0, 9.0 and 10.0, 9.0 and 9.5 or 9.5 and 10.0. In a further embodiment the pH is maintained using a buffer from the group consisting of phosphate buffer, Tris buffer and histidine buffer. Optionally the buffer is at a concentration of 10-200 mM, 50-100 mM, 100-200 mM, 10-50 mM or 50-150 mM. Optionally the buffer is phosphate buffer at 80-120 mM, 80-100 mM or 100 mM.

In one embodiment the pH in step b) is at least, exactly or approximately 2.0, 1.5, 1.0, 0.5, 0.3, 0.2 or 0.1 pH units higher than the pH in step a).

In one embodiment the process of the invention is carried out in a fementor. In an embodiment the pH is increased such that the pH in step b) is higher than the pH of step a). Optionally this increase in pH is achieved by addition of base for instance sodium hydroxide or ammonia.

In a further embodiment the pH of step (b) is maintained between 6.5 and 10.0, 6.5 and 9.5, 6.5 and 9.0, 6.5 and 8.5, 6.5 and 7.5, 6.5 and 7.0, 7.0 and 10.0, 7.0 and 9.5, 7.0 and 9.0, 7.0 and 8.5, 7.0 and 8.0, 7.0 and 7.5, 7.5 and 10.0, 7.5 and 9.5, 7.5 and 9.0, 7.5 and 8.5, 7.5 and 8.0, 8.0 and 10.0, 8.0 and 9.5, 8.0 and 9.0, 8.0 and 8.5, 8.5 and 10.0, 8.5 and 9.5, 8.0 and 9.0, 8.0 and 8.5, 8.5 and 10.0, 8.5 and 9.5, 8.5 and 9.0, 9.0 and 10.0, 9.0 and 9.5 or 9.5 and 10.0 by the addition of base for instance sodium hydroxide or ammonia during step b).

In one embodiment the process of the invention comprises a first substrate feed rate in step a) and a second substrate feed rate in step b) wherein the second substrate feed rate is lower than the first substrate feed rate. In a further embodiment the second substrate feed rate is maintained between 5% and 90%, 20% and 80% or 20% and 30% of the substrate feed rate maintained during step a).

Substrate feed rate (or substrate provision rate) is the rate of substrate addition during the fed-batch and induction phases (ml min$^{-10}$) i.e. does not include any initial non-fed batch phase period of fermentation.

In an embodiment the bacterial toxin is pneumolysin toxin, diphtheria toxin, a tetanus toxin or a pertussis toxin or a point mutated variant thereof. In an embodiment the toxin is diptheria toxoid. In a further embodiment the toxin is CRM 197, optionally this encoded by SEQ ID NO:32. In a further embodiment the bacterial toxin is a fragment or point mutated variant of pneumolysin, diphtheria toxin, tetanus toxin or pertussis toxin.

The bacterial host cell of this process was defined in the section on vectors and host cells. In one embodiment the bacterial host cell is selected from the group consisting of *E. coli, Acinetobacter, Actinobacillus, Bordetella, Brucella, Campylobacter, Cyanobacteria, Enterobacter, Erwinia, Franciscella, Helicobacter, Hemophilus, Klebsiella, Legionella, Moraxella, Neisseria, Pasteurella, Proteus, Pseudomonas, Salmonella, Serratia, Shigella, Treponema, Vibrio,* and *Yersinia.*

In an embodiment the bacterial host cell is a strain of *E. coli*. In a further embodiment the bacterial host cell is a K strain or a B strain of *E. coli*. In a further embodiment the bacterial host cell is a K12 or B834 strain of *E. coli*.

In an embodiment the temperature of step a) is higher than the temperature of step b). In an embodiment step a) of the process of the invention is carried out at a temperature of 20-40° C. Optionally step b) of the process of the invention is carried out at a temperature of 20-28° C., 21-27° C., 22-26° C., 23-24° C., 21-24° C., or 22-23° C.

In a further embodiment expression is induced in step b) by the addition of a sufficient quantity of IPTG (isopropyl-beta-D-thiogalactopyranoside). Optionally this is at a concentration of between 0.1 and 10 mM, 0.1 and 5 mM, 0.1 and 2.5 mM, 0.2 and 10 mM, 0.2 and 5 mM, 0.2 and 2.5 mM, 0.4 and 10 mM, 1 and 10 mM, 1 and 5 mM, 2.5 and 10 mM, 2.5 and 5 mM, 5 and 10 mM.

In one embodiment the optical density $OD_{650}$ of the bacteria is between 0-2.5 or between 0.4-1.5 at induction. The term 'at induction' refers to the point in the process at which an inducing agent such as IPTG is added, this will occur at the very beginning of step b).

A fermentor is any apparatus suitable for the industrial production of bacterial cultures. However this term does not include culture flasks which are typically used for growth of bacteria on a smaller scale. Optionally the fermentor contains 20-500, 50-500, 100-500, 250-500, 400-500, 20-400, 50-400, 100-400, 250-400, 20-250, 100-200, 100-250, 250-300, 300-500, 10-2000, 500-2000, 1000-2000, 1500-2000 or 1000-1500 or around 150 liters of culture.

Optionally the culture in the fermentor is agitated. Agitation is optionally by stirring the culture in the fermentor but may be by any other suitable means, for example by agitation, vibromixer and/or gas bubbling.

In an embodiment the dissolved oxygen level (DO) in the fermentor is (maintained) greater than 5%, 10%, 15%, 16%, 17%, 18%, 19% 20%, 21%, 22%, 23%, 24%, 25% or 30%. In a further embodiment the DO in the fermentor is 5%-50%, 10%-40%, 15%-25% or 17%-22%. A 100% DO is the amount of oxygen present when the medium (in the absence of a culture) is saturated with oxygen following bubbling compressed air through the medium at 28° C. and pressure of 0.5 bar.

The fermentation step may be subject to a large amount of foam production. In order to control foam formation an antifoam agent is optionally added to the fermentor. Optionally a foam probe or mechanical foam breaker is used in the fermentor, this may be used as well as the antifoam agent.

In an embodiment the process for making the bacterial toxin involves removal of a signal peptide from the bacterial toxin within the bacterial host cell to obtain a mature bacterial toxin. Optionally this removal is carried out by host cell machinery. In an embodiment cleavage is performed by the *E. coli* signal peptidase. Optionally the removed signal sequence is cleaved further by signal peptide peptidase.

In an embodiment the process of the invention comprises a further step c) of harvesting the cell paste from the culture.

In an embodiment centrifugation is used to harvest the cells. Optionally this takes place at 5,000-8,000 g, 5,500-7,500 g, 6,000-7,000 g. Optionally this takes place between 4° C.-10° C. 5° C.-9° C., 6° C.-8° C. or 7° C.-8° C.

In a further embodiment the process of the invention comprises a further step of purifying the bacterial toxin, for example as a mature bacterial toxin. In an embodiment this step involves cell disruption and further purification using chromatography and filtration techniques.

In an embodiment cells are disrupted using osmotic shock, mechanical or enzymatic methods. Optionally the mechanical method comprises using a mechanical homogenizer, vortexing, sonication, using a French press or bead milling. Optionally the enzymatic method comprises using lysozyme, zymolase or lysostaphin digestion.

In an embodiment the chromatography technique is affinity chromatography, gel filtration, high pressure liquid chromatography (HPLC) or ion exchange chromatography. Optionally the affinity chromatography uses an affinity tag purification column, an antibody purification column, a lectin affinity column, a prostaglandin purification column or a streptavidin column. Optionally the HPLC uses an ion exchange column, a reverse phase column or a size exclusion column. Optionally the ion exchange column is an anion exchange column or a cation exchange column.

Conjugation

The invention also provides a process for making a conjugate comprising the steps of i) making a bacterial toxin using the process of the invention, and b) conjugating the bacterial toxin of step ii) to an antigen.

In an embodiment the antigen is a bacterial saccharide. For example the bacterial saccharide is a capsular saccharide from a bacterium selected from the group consisting of *S. pneumoniae, H. influenzae, N. meningitidis,* group *B Streptococcus,* group *A Streptococcus, Salmonella Vi,* enterococci and *S. aureus.* As defined herein a "saccharide" may be either an oligosaccharide or a polysaccharide.

The saccharide conjugates present in the immunogenic compositions of the invention may be prepared by any known coupling technique. The conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). Preferably, the cyanate ester (optionally made by CDAP chemistry) is coupled with hexane diamine or ADH and the amino-derivatised saccharide is conjugated to the carrier protein using carbodiimide (e.g. EDAC or EDC) chemistry via a carboxyl group on the protein carrier. Such conjugates are described in PCT published application WO 93/15760 Uniformed Services University and WO 95/08348 and WO 96/29094.

Other suitable techniques use carbodiimides, hydrazides, active esters, norborane, p-nitrobenzoic acid, N-hydroxysuccinimide, S—NHS, EDC, TSTU. Many are described in WO 98/42721. Conjugation may involve a carbonyl linker which may be formed by reaction of a free hydroxyl group of the saccharide with CDI (Bethell et al J. Biol. Chem. 1979, 254; 2572-4, Hearn et al J. Chromatogr. 1981. 218; 509-18) followed by reaction with a protein to form a carbamate linkage. This may involve reduction of the anomeric terminus to a primary hydroxyl group, optional protection/deprotection of the primary hydroxyl group' reaction of the primary hydroxyl group with CDI to form a CDI carbamate intermediate and coupling the CDI carbamate intermediate with an amino group on a protein.

The conjugates can also be prepared by direct reductive amination methods as described in U.S. Pat. No. 4,365,170 (Jennings) and U.S. Pat. No. 4,673,574 (Anderson). Other methods are described in EP-0-161-188, EP-208375 and EP-0-477508.

A further method involves the coupling of a cyanogen bromide (or CDAP) activated saccharide derivatised with adipic acid dihydrazide (ADH) to the protein carrier by Carbodiimide condensation (Chu C. et al Infect. Immunity, 1983 245 256), for example using EDAC.

In an embodiment, a hydroxyl group (preferably an activated hydroxyl group for example a hydroxyl group activated to make a cyanate ester [e.g. with CDAP]) on a saccharide is linked to an amino or carboxylic group on a protein either directly or indirectly (through a linker). Where a linker is present, a hydroxyl group on a saccharide is preferably linked to an amino group on a linker, for example by using CDAP conjugation. A further amino group in the linker for example ADH) may be conjugated to a carboxylic acid group on a protein, for example by using carbodiimide chemistry, for example by using EDAC. In an embodiment, the pneumococcal capsular saccharide(s) is conjugated to the linker first before the linker is conjugated to the carrier protein. Alternatively the linker may be conjugated to the carrier before conjugation to the saccharide.

In general the following types of chemical groups on a protein carrier can be used for coupling/conjugation:

A) Carboxyl (for instance via aspartic acid or glutamic acid). In one embodiment this group is linked to amino groups on saccharides directly or to an amino group on a linker with carbodiimide chemistry e.g. with EDAC.

B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.

C) Sulphydryl (for instance via cysteine). In one embodiment this group is linked to a bromo or chloro acetylated saccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or NH2. Aldehyde groups can be generated after different treatments known in the art such as: periodate, acid hydrolysis, hydrogen peroxide, etc.

Direct Coupling Approaches:
Saccharide-OH+CNBr or CDAP→cyanate ester+NH2-Prot→conjugate
Saccharide-aldehyde+NH2-Prot→Schiff base+NaCNBH3→conjugate
Saccharide-COOH+NH2-Prot+EDAC→conjugate
Saccharide-NH2+COOH-Prot+EDAC→conjugate Indirect Coupling via Spacer (Linker) Approaches:
Saccharide-OH+CNBr or CDAP→cyanate ester+NH2-NH2→saccharide-NH2+COOH-Prot+EDAC→conjugate
Saccharide-OH+CNBr or CDAP→cyanate ester+NH2-SH→saccharide-SH+SH-Prot (native Protein with an exposed cysteine or obtained after modification of amino groups of the protein by SPDP for instance)→saccharide-S—S-Prot
Saccharide-OH+CNBr or CDAP→cyanate ester+NH2-SH→saccharide-SH+maleimide-Prot (modification of amino groups)→conjugate
Saccharide-OH+CNBr or CDAP→cyanate ester+NH2-SH→Saccharide-SH+haloacetylated-Prot→Conjugate
Saccharide-COOH+EDAC+NH2-NH2→saccharide-NH2+EDAC+COOH-Prot→conjugate
Saccharide-COOH+EDAC+NH2-SH→saccharide-SH+SH-Prot (native Protein with an exposed cysteine or obtained after modification of amino groups of the protein by SPDP for instance)→saccharide-S—S-Prot
Saccharide-COOH+EDAC+NH2-SH→saccharide-SH+maleimide-Prot (modification of amino groups)→conjugate
Saccharide-COOH+EDAC+NH2-SH→Saccharide-SH+haloacetylated-Prot→Conjugate
Saccharide-Aldehyde+NH2-NH2→saccharide-NH2+EDAC+COOH-Prot→conjugate Note: instead of EDAC above, any suitable carbodiimide may be used.

In summary, the types of protein carrier chemical group that may be generally used for coupling with a saccharide are amino groups (for instance on lysine residues), COOH groups (for instance on aspartic and glutamic acid residues) and SH groups (if accessible) (for instance on cysteine residues.

Vaccine or Immunogenic Compositions of the Invention

The present invention further provides a process for manufacturing a vaccine or immunogenic composition comprising the steps of
  A. making a bacterial toxin or conjugate using the process of the invention and;
  B. mixing the bacterial toxin or conjugate thereof with a pharmaceutically acceptable excipient.

The vaccine or immunogenic composition produced by this process may additionally comprise antigens from further bacterial species. In one embodiment the vaccine or immunogenic composition may comprise antigens selected from S.

*pneumoniae, H. influenzae, N. meningitidis, E. coli, M. cattarhalis, tetanus, diphtheria, pertussis, S. epidermidis, enterococci*, or *S. aureus*.

In a further step the polypeptides of the invention may be mixed with an adjuvant. The choice of a suitable adjuvant to be mixed with bacterial toxins or conjugates made using the processes of the invention is within the knowledge of the person skilled in the art. Suitable adjuvants include an aluminium salt such as aluminium hydroxide gel or aluminum phosphate or alum, but may also be other metal salts such as those of calcium, magnesium, iron or zinc, or may be an insoluble suspension of acylated tyrosine, or acylated sugars, cationically or anionically derivatized saccharides, or polyphosphazenes.

The vaccine preparations containing immunogenic compositions of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance pneumococcal saccharide conjugates could be administered separately, at the same time or 1-2 weeks after the administration of the any bacterial protein component of the vaccine for optimal coordination of the immune responses with respect to each other). In addition to a single route of administration, 2 different routes of administration may be used. For example, saccharides or saccharide conjugates may be administered IM (or ID) and bacterial proteins may be administered IN (or ID). In addition, the vaccines of the invention may be administered IM for priming doses and IN for booster doses.

The content of toxins in the vaccine will typically be in the range 1-100 μg, preferably 5-50 μg, most typically in the range 5-25 μg. Following an initial vaccination, subjects may receive one or several booster immunizations adequately spaced.

Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

EXAMPLES

Example 1

Design of CRM197-Signal Sequence Constructs

Plasmids containing a sequence encoding an N-terminal signal sequence fused to the CRM197 toxoid were created using standard molecular biology techniques. Thirteen different signal sequences were used (table 2); these were selected from the GenEMBL database.

TABLE 2

| Signal sequence | SEQ ID NO nucleotide | SEQ ID NO Amino acid | Origin |
|---|---|---|---|
| PhtE | 1 | 2 | *S. pneumoniae* |
| SipA | 3 | 4 | *Group B Strep* |
| OmpA | 5 | 6 | *E.coli* |
| NspA | 7 | 8 | *N. meningitidis* |
| TorT | 9 | 10 | *E.coli* |
| SfmC | 11 | 12 | *E.coli* |
| FocC | 13 | 14 | *E.coli* |
| Ccmh | 15 | 16 | *E.coli* |
| Yra1 | 17 | 18 | *E.coli* |
| ToIB | 19 | 20 | *E.coli* |
| NikA | 21 | 22 | *E.coli* |
| Figl | 23 | 24 | *E.coli* |
| DsbA | 25 | 26 | *E.coli* |

The first construct was created from three plasmids (see FIG. 1). Plasmid A, created by Geneart, contained the DsbA signal sequence (SEQ ID NO:25) 3' to a sequence encoding an N-terminal fragment of CRM197 (amino acids 1-206 of SEQ ID NO 32). This plasmid was cloned into the pET26b backbone plasmid (Novagen) by digestion of both plasmids using NdeI and SacI restrictions enzymes followed by ligation. Plasmid B, created by Geneart, contained a C-terminal fragment of CRM197 (amino acids 206-533 of SEQ ID NO 32). this was cloned into the pET26b backbone using restriction with AatII and XhoI restriction enzymes, the resulting plasmid was named pRIT16668. This construct contains the signal sequence from DsbA up to the signalase binding site, followed by two amino acids from DsbA found after the signalase binding sequence, a further two amino acids from the restriction enzyme binding site, and finally CRM197 missing the first two amino acids. This means that when these constructs are expressed the protein produced after periplasmic expression and removal of the signal sequence by signalase contains CRM197 missing the first two amino acids but with an extra four amino acids from DsbA and the restriction site.

The pRIT16668 plasmid contains NdeI and AgeI restrictions sites flanking the DsbA signal sequence.

Plasmids containing the 12 other signal sequences were created by digesting plasmid pRIT16668 with NdeI and AgeI to remove the DsbA signal sequence. Hybridized oligonucleotides encoding each of the other 12 signal sequences were, one at a time, ligated between these two sites.

The resulting plasmids were transformed into Novablue chemically competent cells (Novagen cat 70181-3, used as recommended by manufacturer). The presence of the correct insert was confirmed for each plasmid by sequencing. The plasmids were then transformed individually into B834(DE3) chemically competent cells (Novagen cat 69041-3HMS174 (DE3) chemically competent cells or alternatively BLR (DE3) chemically competent cells (Novagen cat 69053-3, used as recommended by manufacturer), for expression.

Example 2

Design of a CRM197 Construct for Cytoplasmic Expression (Lacking the Periplasmic Signal Sequence)

In this experiment, a plasmid similar to those created in Example 1 but lacking the periplasmic signal sequence was created. This design process is summarised in FIG. 2. Firstly the CRM197 sequence (SEQ ID NO:31) was amplified by standard PCR techniques using two primers which were named MDSCRM1 (SEQ ID NO:27) and MDSCRM2 (SEQ ID NO:28) and pRIT16668 as the template (the temperature cycles used were (94° C. 2'-55° C. 2'-72° C. 2'30) X 25-72° C. 10'-end 4° C.).

This fragment was inserted into plasmid pRIT16668 in place of the CRM197 signal sequence insert. This was achieved using standard molecular biology techniques through digestion of the PCR product and pRIT16668 with the restriction enzymes NdeI and XhoI. The resulting plasmid contains the mature CRM197 sequence (SEQ ID NO:31) but contains no signal sequence and was named pRIT16669.

The resulting plasmids were transformed into Novablue chemically competent cells (Novagen cat 70181-3, used as recommended by manufacturer). The presence of the correct insert was confirmed for each plasmid by sequencing. The plasmids were then transformed into B834(DE3) chemically competent cells (Novagen cat 69041-3, used as recommended by manufacturer) for expression.

Example 3

Design of an Optimal Signal Sequence-CRM197 Construct

The signal sequence FIgI was selected for use to create an improved construct. The cloning process followed is summarized in FIG. 3.

A region of DNA containing the FIgI signal sequence fused to the N-terminal part of the CRM197 sequence was amplified using standard PCR techniques. Two primers were used, primers named FIgI c-CRMopt3e (SEQ ID NO:29) and MDSCRM906NC (SEQ ID NO: 30) primer using pRIT16669 as template with cycling (94° C. 2'(94° C. 1'-60° C. 1'-72° C. 2'30)X3 (94° C. 1'-58° C. 1'-72° C. 2'30)X3 (94° C. 1'-56° C. 1'-72° C. 2'30)X3(94° C. 1'-54° C. 1'-72° C. 2'30)X20 72° C. 10'-end 4° C.).

This fragment was inserted into plasmid pRIT16669 using standard molecular biology techniques through digestion of the PCR product and plasmid pRIT16669 with the restriction enzymes NdeI and AatII. The resulting plasmid contains the complete mature N-terminus of CRM197(SEQ ID NO:31) and the FIgI signal sequence terminating at the signalase binding site (SEQ ID NO:23) and was named pRIT16681.

The resulting plasmids were transformed into Novablue chemically competent cells (Novagen cat 70181-3, used as recommended by manufacturer). The presence of the correct insert was confirmed for each plasmid by sequencing. The plasmids were then transformed into B834(DE3) chemically competent cells (Novagen cat 69041-3) cells for expression.

Example 4

Expression of DsbA Signal Sequence-CRM197 Construct

In this experiment, cells transformed with the DsbA signal sequence constructs created in Example 1 were cultured and expression induced. Pre-cultures (3 ml) of the B834(DE3), HMS174(DE3) and BLR(DE3) recombinant strain were grown in LBT medium supplemented with 1% glucose in the presence of kanamycin (50 μg/ml) overnight at 37° C. under agitation. The next day samples of this preculture were added to 20 ml LBT medium with 50 μg/ml of kanamycin after the optical density $OD_{620}$ of the medium reached 0.1. These cells were allowed to grow at 30° C. under agitation. In this plasmid, CRM197 expression is under the control of the lac operator, therefore expression of the encoded CRM197 can be induced on addition of isopropyl-beta-D thiogalactopyranoside (IPTG). When the optical density reached 0.6 induction with IPTG (added until there is a final concentration of 1 mM) was carried out and the culture was allowed to grow further, for 3 h at 30° C.

The level of CRM197 expression was evaluated by running the total bacterial cell product on an SDS-PAGE gel (Novex Tris-glycine 10-20%) and staining with Coomassie brilliant blue. A Western blot was carried out using mouse anti-DTPa polyclonal antibody staining with NBT-BCIP.

FIG. 4 describes the results of this experiment. The Coomassie gel shows no difference in expression profile between the induced and non-induced cultures. The Western blot demonstrates a lack of CRM197 in both the induced and non-induced cultures. There is no or little periplasmic CRM197 expressed under these conditions.

Example 5

Optimisation of pH and Temperature Conditions and Expression Analysis of the Constructs The steps in example 4 were repeated; however in this case 100 mM of $K_2HPO_4/KH_2PO_4$ buffer was added to the culture before induction such that the medium was buffered to pH7.5. Expression was induced by addition of 1 mM IPTG and the culture was allowed to grow overnight at either 23° C. or 30° C. The level of protein expressed in the supernatant and pellet was evaluated using Coomassie staining and Western blot techniques as described in Example 4.

With regard to the post-translational signal sequences, the expression level of CRM197 was very high for the OmpA signal sequence, however the protein is cleaved to form a protein of around 27 kDa. This truncated form is cell associated (not found in either the periplasmic release fraction or in the culture medium). With regard to the NspA signal sequence, expression is positive but a low level of mature CRM197 is obtained.

With regard to the co-translational sequences, the expression level is high with FIgI and SipA signal sequences, however the CRM197 produced is not fully matured. Expression with the NikA signal sequence leads to expression of mature protein. The global expression level is lower than with FIgI and SipA signal sequence but is still detectable in the total extract by Coomassie staining.

Example 6

Expression Analysis of the CRM197 Cytoplasmic Expression Constructs

DE3 cells were transformed with the plasmids produced in example 2, cultured and expression of CRM197 induced as described in Example 4. The CRM197 expression level was evaluated by running the product of the total bacterial cell on an SDS-PAGE gel and using Coomassie blue staining and western blot techniques as described in Example 4. Bacterial extracts were performed by one shot technic (Constant system) in standard PBS buffer. After centrifugation, the soluble and insoluble fractions obtained were loaded onto a gel.

The results of this experiment are presented in FIG. 6. The gene is well expressed in these strains nevertheless a substantial part of the protein is insoluble and remains in pellet. Furthermore cytoplasmic expression leads to apparent lower molecular weight proteins appearing on the gel.

Example 7

Expression Analysis of the Optimised FlgI Construct

BLR(DE3) *E. coli* cells were transformed with the construct produced in example 3, cultured and expression induced as described in the optimised protocol of example 5. In addition some sample cells were grown without the addition of 100 mM $K_2HPO_4/KH_2PO_4$ buffer. Similarly the level of protein expressed was evaluated using Coomassie staining and Western blot techniques as described in Example 4. At induction temperature was maintained at either 23° C. or 30° C. and samples were taken at the time of induction, 2 hours after induction, 4 hours after induction and after overnight induction.

The results of this experiment are shown in FIG. 7. The Western blot demonstrates an easily detectable level of expression of CRM197 with buffer at 23° C. The levels of protein expression in the cells which were not buffered during the induction phase were observed to be lower.

Example 8

*Escherichia Coli* B2355 Pre-Culture

A pre-culture was prepared using a frozen seed culture of *Escherichia coli* strain B2355. This strain is a B834(DE3) strain transformed with a pET26b derivative containing a sequence coding for a fusion protein between the signal peptide of FlgI from *E. coli* and the mature part of CRM197 (this is plasmid pRIT16681 described in FIG. 3 and example 3). The seed culturability was determined as approximately $1 \times 10^{10}$ colony forming units per ml.

The seed culture was thawed to room temperature and 400 µl were used to inoculate a 2 liter Erlenmeyer flask containing 400 ml of preculture medium (adapted from Zabriskie et al. (J. Ind. Microbiol. 2:87-95 (1987))).

The inoculated flask was then incubated at 37° C. (±1° C.) and 200 rpm. The pre-culture was stopped when the optical density at 650 nm ($OD_{650\,nm}$) reached 2.50, (around 6 h of incubation). The pre-culture was used to inoculate medium in a fermenter as soon as the culture was stopped (example 9).

Example 9

20 L Scale Fedbatch Fermentation

Method

A 20 liter fermenter (Biolafitte) was used. Nine liters of batch phase medium were aseptically transferred into the fermenter (adapted from Zabriskie et al. (J. Ind. Microbiol. 2:87-95 (1987)). The pH of the medium was readjusted to 6.8 with base addition. 3 ml of undiluted irradiated antifoam (SAG 471) was also added to the fermenter. The temperature (28° C.), head pressure (0.5 bar), aeration rate (20 liters sparged air per minute) and initial agitation speed (300 rpm) were then set prior to inoculation. The level of dissolved oxygen in these conditions was 100%. The head pressure and aeration rate were maintained at a constant level during the fermentation.

Inoculation was achieved by the addition of 18 ml of pre-culture (prepared as described in Example 8).

During batch phase (0-15 h), the temperature was maintained at 28° C. The level of dissolved oxygen was set at 20%. The level of dissolved oxygen (DO) was regulated by increasing stirring when the DO fell below 20%. Glucose exhaustion resulted in an increase in DO and a concomitant decrease in stirring.

After 15 h fermentation, additional substrate was added according to the following feed addition profile:

TABLE 3

| Fermentation time (h) | Additional substrate feed rate (ml/min) | Cumulative weight fed (g) |
|---|---|---|
| 0 | 0.000 | 0 |
| 1 | 0.000 | 0 |
| 2 | 0.000 | 0 |
| 3 | 0.000 | 0 |
| 4 | 0.000 | 0 |
| 5 | 0.000 | 0 |
| 6 | 0.000 | 0 |
| 7 | 0.000 | 0 |
| 8 | 0.000 | 0 |
| 9 | 0.000 | 0 |
| 10 | 0.000 | 0 |
| 11 | 0.000 | 0 |
| 12 | 0.000 | 0 |
| 13 | 0.000 | 0 |
| 14 | 0.000 | 0 |
| 15 | 0.000 | 0 |
| 16 | 0.600 | 21 |
| 17 | 1.150 | 81 |
| 18 | 1.150 | 161 |
| 19 | 1.150 | 241 |
| 20 | 1.150 | 321 |
| 21 | 1.150 | 400 |
| 22 | 1.150 | 480 |
| 23 | 1.150 | 560 |
| 24 | 1.150 | 639 |
| 25 | 1.150 | 719 |
| 26 | 1.150 | 799 |
| 27 | 1.150 | 878 |
| 28 | 1.150 | 958 |
| 29 | 1.150 | 1038 |
| 30 | 1.150 | 1117 |
| 31 | 1.150 | 1197 |
| 32 | 1.150 | 1277 |
| 33 | 1.150 | 1357 |
| 34 | 1.150 | 1436 |
| 35 | 1.150 | 1516 |
| 36 | 1.150 | 1596 |
| 37 | 1.150 | 1675 |
| 38 | 1.150 | 1755 |
| 39 | 1.150 | 1835 |
| 40 | 1.150 | 1914 |
| 41 | 1.150 | 1994 |
| 42 | 1.150 | 2074 |
| 43 | 1.150 | 2153 |
| 44 | 1.150 | 2233 |
| 45 | 1.150 | 2313 |
| 46 | 1.150 | 2393 |
| 47 | 0.325 | 2444 |
| 48 | 0.325 | 2466 |
| 49 | 0.325 | 2489 |
| 50 | 0.325 | 2511 |
| 51 | 0.325 | 2534 |
| 52 | 0.325 | 2556 |
| 53 | 0.325 | 2579 |
| 54 | 0.325 | 2601 |
| 55 | 0.325 | 2624 |
| 56 | 0.325 | 2646 |
| 57 | 0.325 | 2669 |
| 58 | 0.325 | 2691 |
| 59 | 0.325 | 2714 |
| 60 | 0.325 | 2736 |
| 61 | 0.325 | 2759 |
| 62 | 0.325 | 2782 |
| 63 | 0.325 | 2804 |
| 64 | 0.325 | 2827 |
| 65 | 0.325 | 2849 |
| 66 | 0.325 | 2872 |
| 67 | 0.325 | 2894 |

TABLE 3-continued

| Fermentation time (h) | Additional substrate feed rate (ml/min) | Cumulative weight fed (g) |
|---|---|---|
| 68 | 0.325 | 2917 |
| 69 | 0.325 | 2939 |
| 70 | 0.325 | 2962 |
| 71 | 0.325 | 2984 |
| 72 | 0.325 | 3007 |

During the fed-batch phase (15-46 h), the pH was maintained at 6.8 by addition of base, the temperature was regulated at 28° C., and the DO level was maintained at 20% through control of the stirring rate.

At 46 hours IPTG was added to a final concentration of 1 mM to induce the bacteria. In addition the pH is gradually increased after 46 hours by addition of base, and the temperature was decreased to 23° C. (these changes are required for high levels of periplasmic expression). The pH and temperature were maintained during the whole induction phase (46-72 h). The DO level was maintained at 20% by controlling the stirring rate.

At the end of the induction phase (72 h), cell paste was collected by centrifugation (6,500×g, 4° C. for 1 h), and stored at −20° C.

Periplasmic extraction was performed by osmotic shock using a procedure adapted from Chen et al. (Biochem. Eng. J. 19:211-215 (2004)). CRM197 content in the periplasmic and cytoplasmic fractions were assayed by Elisa.

FIG. 8 shows a typical fermentation profile with the process parameters monitored during 20 L-scale fed-batch fermentation.

At the end of fermentation, periplasmic CRM197 productivity was assayed by Elisa:

TABLE 4

| Periplasmic | Cytoplasmic | Secretion efficiency |
|---|---|---|
| 3180 mg/L | 394 mg/L | 87% |

This technique demonstrated unprecedented levels of expression and efficiency of secretion.

Example 10

Determination of the Optimum Feed Rates and Temperatures to be Used During the Induction Phase In this experiment response-surface methodology (J. ind. Microbiol. Biotechnol. 37:195-204 (2010)) was used to determine optimal values for three parameters, in order to maximize periplasmic production of a recombinant protein. The three fermentation parameters investigated were the pH during the growth phase, the pH during induction and the feed rate during induction. Values for these three parameters were chosen according to a Doehlert uniform shell design (Doehlert (Applied Statistics 19:231-239 (1970))). Fifteen fermentations were carried out using the values described in table 5.

Figure 1:
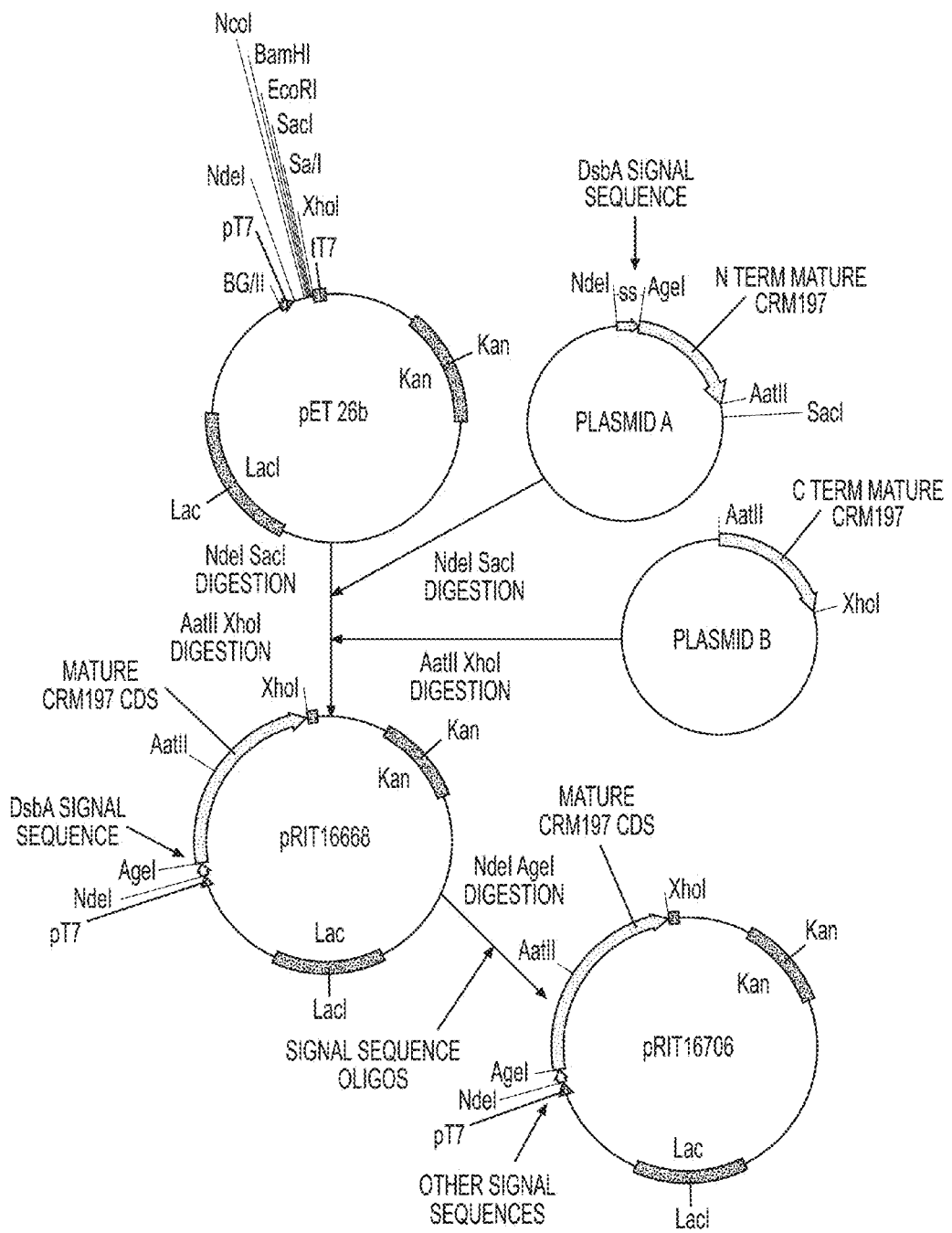
FIG. 1—Overview of the cloning process to produce the CRM197-signal sequence constructs. A section of DNA encoding a signal sequence fused to the N-terminus of CRM197 is cut from plasmid A by NdeI and SacI digestion. The C-terminal sequence of CRM197 SEQ ID NO:31 is cut from plasmid B by AatII and XhoI digestion. These two sequences are spliced into a pET26b vector by digestion of the pET26b vector with NdeI, SacI, AatII and XhoI and ligation using DNA ligase. The resulting vector (pRIT16668) was used to produce the other signal sequence-CRM197 constructs by digesting plasmids containing the signal sequences and the pRIT16668 vector with AgeI and NdeI and splicing these together using DNA ligase.
Figure 2:
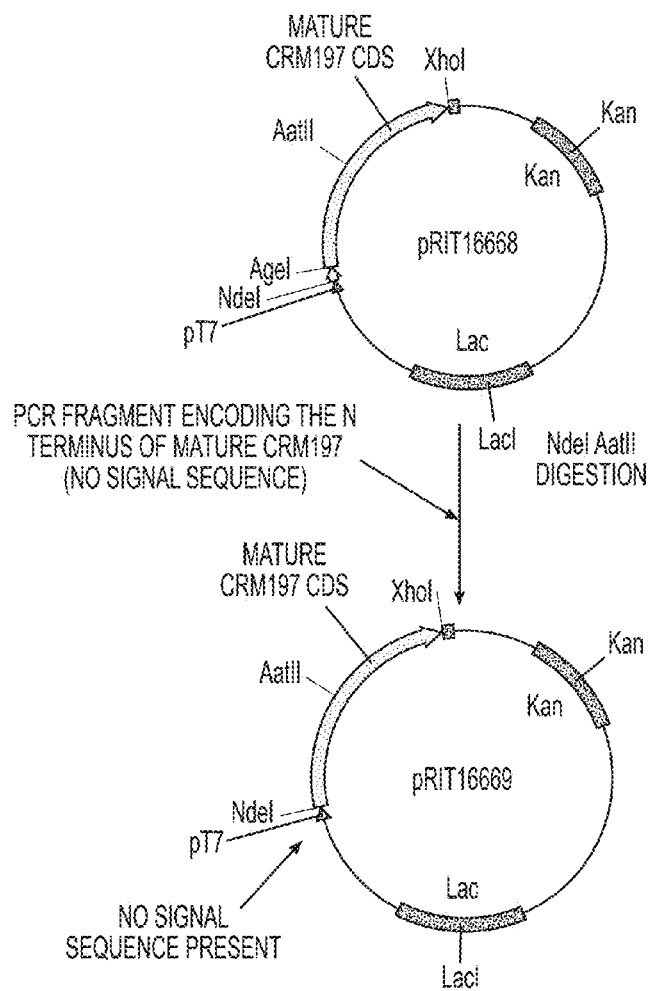
FIG. 2—Overview of the cloning process to produce constructs containing the CRM197 sequence without an N-terminal signal sequence (pRIT16669). This was carried out by inserting a PCR fragment encoding CRM197 into pRIT16668 using NdeI and AatII digestion followed by ligation.
Figure 3:
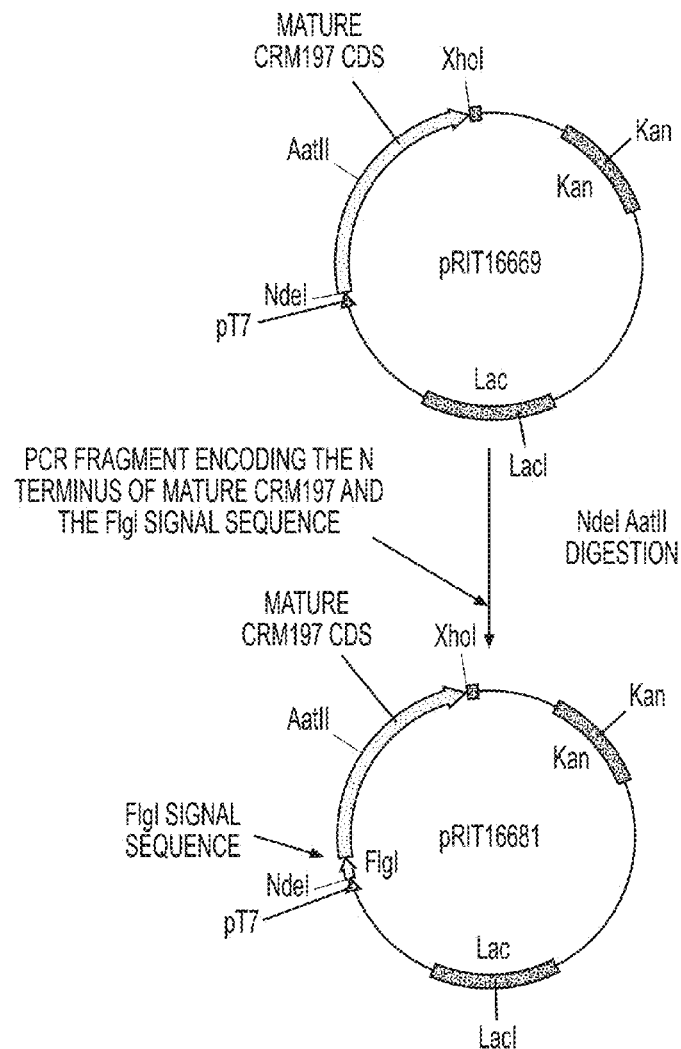
FIG. 3—Overview of the cloning process to produce constructs containing the FIgI signal sequence. This was carried out by inserting a PCR fragment encoding the CRM197 and the FIgI signal sequence (SEQ ID NO: 23) into pRIT16669 using NdeI and AatII digestion followed by ligation. This produced the plasmid pRIT16681.

The fermentations were carried out using strain B2284, this is a strain of BLR (DE3) cells transformed with a pET26b derivative containing a sequence coding for a fusion protein between the signal peptide of FlgI from *E. coli* and the mature part of CRM197 (this is plasmid pRIT16681 described in FIG. 3 and example 3).

For each fermentation, the seed culture was thawed to room temperature and 500 μl was used to inoculate a 2 liter Erlenmeyer flask containing 400 ml of preculture medium (adapted from Zabriskie et al. (J. Ind. Microbiol. 2:87-95 (1987))).

The inoculated flask was then incubated at 37° C. (±1° C.) and 200 rpm. The pre-culture was stopped when the optical density at 650 nm ($OD_{650\,nm}$) reached around 2.5, (around 6 h of incubation). The pre-culture was used to inoculate medium in a fermenter as soon as the culture was stopped (adapted from Zabriskie et al. (J. Ind. Microbiol. 2:87-95 (1987)).

A 20 liter fermenter (Biolafitte) was used. Nine liters of batch phase medium were aseptically transferred into the fermenter. The pH of the medium was readjusted to the target value (Table 5) with base addition. 3 ml of undiluted irradiated antifoam (SAG 471) was also added to the fermenter. The temperature (28° C.), head pressure (0.5 bar), aeration rate (20 liters sparged air per minute) and initial agitation speed (300 rpm) were then set prior to inoculation. The level of dissolved oxygen (DO) in these conditions was 100%. The head pressure and aeration rate were maintained at a constant level during the fermentation.

Inoculation was achieved by the addition of 15-20 ml of pre-culture.

During batch phase (0-15 h), the temperature was maintained at 28° C. The level of dissolved oxygen was set at 20% and regulated by increasing stirring when the DO fell below 20%

During the fed-batch phase (15-46 h), the pH was maintained according to one of the conditions described in table 5 by addition of base. The temperature was regulated at 28° C. The stirring rate was maintained at a constant setpoint (maximum 800 rpm), and the DO level was maintained at 20% by automatic addition of concentrated feed solution (adapted from Zabriskie et al. (J. Ind. Microbiol. 2:87-95 (1987)) when the DO increased above 20%.

When the culture reached an $OD_{650\,nm}$ around 90, the pH setpoint was modified according to one of the conditions described in table 5 by base or acid addition and the temperature was decreased to 23° C. Once these conditions were achieved IPTG was added to a final concentration of 1 mM. The pH and temperature were maintained during the whole induction phase (24 h). A constant substrate feed rate was used during the whole induction phase, according to one of the conditions described in table 5. The DO level was maintained at 20% by controlling the stirring rate.

At the end of the induction phase, cell paste was collected by centrifugation (typically 6,500×g, 4° C. for 1 h), and stored at −20° C.

Periplasmic extraction was performed by osmotic shock using a procedure adapted from Chen et al. (Biochem. Eng. J. 19:211-215 (2004)). CRM197 content in the periplasmic and cytoplasmic fractions were assayed by Elisa (table 6).

TABLE 5

| | pH | | Feed rate during | OD650 nm | |
|---|---|---|---|---|---|
| Culture No. | before induction | during induction | induction (ml/min) | at induction | end of fermentation |
| CDT337 | 7.0 | 7.8 | 1.10 | 93.0 | 104.0 |
| CDT338 | 7.0 | 7.8 | 0.28 | 93.0 | 102.4 |
| CDT341 | 7.0 | 8.7 | 0.89 | 94.4 | 40.0 |
| CDT342 | 7.0 | 6.9 | 0.48 | 89.2 | 98.0 |
| CDT344 | 7.0 | 6.9 | 0.89 | 90.0 | 89.0 |
| CDT345 | 7.0 | 8.7 | 0.48 | 92.8 | 42.0 |
| CDT348 | 7.0 | 7.8 | 0.69 | 89.2 | 97.6 |
| CDT349 | 7.0 | 7.8 | 0.69 | 96.0 | 109.0 |
| CDT360 | 7.4 | 8.1 | 0.89 | 88.4 | 98.8 |
| CDT351 | 6.6 | 7.5 | 0.48 | 89.2 | 99.0 |
| CDT354 | 6.6 | 7.5 | 0.89 | 89.0 | 93.6 |
| CDT355 | 6.6 | 8.4 | 0.69 | 87.0 | 40.0 |
| CDT357 | 7.4 | 7.1 | 0.48 | 84.8 | 88.8 |

TABLE 5-continued

|  | pH | | Feed rate during | OD650 nm | |
|---|---|---|---|---|---|
| Culture No. | before induction | during induction | induction (ml/min) | at induction | end of fermentation |
| CDT358 | 7.4 | 7.2 | 0.69 | 84.0 | 86.4 |
| CDT358 | 7.0 | 7.8 | 0.69 | 94.8 | 108.0 |

TABLE 6

| Culture no. | pH before induction | pH during induction | Feed rate during induction (ml/min) | CRM197 (mg/L by Elisa) | |
|---|---|---|---|---|---|
| | | | | Periplasmic | Cytoplasmic |
| CDT337 | 7.0 | 7.8 | 1.10 | 1500 | 422 |
| CDT338 | 7.0 | 7.8 | 0.28 | 921 | 357 |
| CDT341 | 7.0 | 8.7 | 0.89 | 13 | 11 |
| CDT342 | 7.0 | 6.9 | 0.48 | 1058 | 341 |
| CDT344 | 7.0 | 6.9 | 0.89 | 822 | 275 |
| CDT345 | 7.0 | 8.7 | 0.48 | 10 | 20 |
| CDT348 | 7.0 | 7.8 | 0.69 | 1166 | 558 |
| CDT349 | 7.0 | 7.8 | 0.69 | 889 | 652 |
| CDT360 | 7.4 | 8.1 | 0.89 | 77 | 50 |
| CDT351 | 6.6 | 7.5 | 0.48 | 1533 | 427 |
| CDT354 | 6.6 | 7.5 | 0.89 | 803 | 595 |
| CDT355 | 6.6 | 8.4 | 0.69 | 20 | 32 |
| CDT357 | 7.4 | 7.1 | 0.48 | 54 | 29 |
| CDT358 | 7.4 | 7.2 | 0.69 | 681 | 310 |
| CDT359 | 7.0 | 7.8 | 0.69 | 1523 | 685 |

Based on the results from the 15 fermentations, the NEMROD-W software (LPRAI, Marseille, France) was used to model the production of CRM197 in the periplasmic and cytoplasmic fractions.

As shown in FIG. 10, the production of periplasmic CRM197 is maximal at low feed rates during induction (FIG. 10a), while the accumulation of CRM197 inside the cell is maximal at higher feed rates (FIG. 10b). The difference in feed rate optima for the production of periplasmic or cell-associated CRM197 allows for defining conditions that selectively improve the production of periplasmic CRM197. A pH increase at induction is also required for efficient production of periplasmic CRM197 (FIG. 10a).

Table 7 below describes the optimum pH during growth, the optimum pH during induction and the optimum feed rate, as obtained using the NEMROD-W software.

TABLE 8

| Parameter | Value |
|---|---|
| pH during growth | 6.8 |
| pH during induction | 7.5 |
| Feed rate during induction | 0.330 ml min$^{-1}$ |

Optimising the pH and feed rate conditions led to optimal secretion of CRM97 into the periplasm.

---

The invention claimed is:

1. A polynucleotide comprising a 5' signal sequence portion and a 3' toxin portion wherein:
   (a) the 3' toxin portion encodes a mature bacterial toxin polypeptide having an amino acid sequence at least 90% identical to SEQ ID NO: 32; and
   (b) the 5' signal sequence portion encodes a polypeptide having an amino acid sequence capable of directing transport of said bacterial toxin polypeptide to the bacterial periplasm when expressed in a baterial host cell, and wherein the 5' signal sequence is not derived from *C. diphtheriae*.

2. The polynucleotide of claim 1 wherein the 3' toxin portion encodes a polypeptide having the amino acid sequence of SEQ ID NO: 32.

3. The polynucleotide of claim 1 wherein the 3' toxin portion comprises SEQ ID NO: 31.

4. The polynucleotide of claim 1 wherein the 5' signal sequence portion encodes
   (i) any one of SEQ ID NO: 2, 4, 6, 8, 10, 12, 14, 16, 18, 20, 22, 24, or 26;
   (ii) variants of SEQ ID NO: 2, 4, 6, 8, 10, 12, 14, 16, 18, 20, 22, 24, or 26 containing 1, 2 or 3 point mutations, insertions or deletions, which variants are capable of directing transport of said bacterial toxin polypeptide to the periplasm of said bacterial host cell, or
   (iii) fragments of at least 10 amino acids of SEQ ID NO: 2, 4, 6, 8, 10, 12, 14, 16, 18, 20, 22, 24, or 26, which fragments are capable of directing transport of said bacterial toxin polypeptide to the periplasm of said bacterial host cell.

5. The polynucleotide of claim 1 wherein the 5' signal sequence portion encodes
   (i) SEQ ID NO: 24;
   (ii) variants of SEQ ID NO: 24 containing 1, 2 or 3 point mutations, insertions or deletions, which variants are capable of directing transport of said bacterial toxin polypeptide to the periplasm of said bacterial host cell; or
   (iii) fragments of at least 10 amino acids of SEQ ID NO: 24, which fragments are capable of directing transport of said bacterial toxin polypeptide to the periplasm of said bacterial host cell.

6. A polynucleotide comprising a 5' signal sequence portion and a 3' toxin portion, wherein:
   (i) the 3' toxin portion encodes a mature bacterial toxin polypeptide having an amino acid sequence at least 90% identical to SEQ ID NO:32; and
   (ii) the 5' signal sequence portion encodes a polypeptide having an acid sequence capable of directing transport of said bacterial toxin polypeptide to the bacterial periplasm when expressed in a bacterial host cell, and wherein the 5' signal sequence is not derived from *C. diphtheria*, and wherein the encoded polypeptide has an amino acid sequence selected from:
      (a) SEQ ID NO: 2, 4, 6, 8, 10, 12, 14, 16, 18, 20, 22, 24, and 26;
      (b) variants of SEQ ID NO: 2, 4, 6, 8, 10, 12, 14, 16, 18, 20, 22, 24, or 26, varying from the corresponding sequences by 1, 2 or 3 point mutations, amino acid insertions or amino acid deletions, which variants are capable of directing transport of said bacterial toxin polypeptide to the periplasm of said bacterial host cell; and
      (c) fragments of at least 10 amino acids of SEQ ID NO: 2, 4, 6, 8, 10, 12, 14, 16, 18, 20, 22, 24, or 26, which fragments are capable of directing transport of said bacterial toxin polypeptide to the periplasm of said bacterial host cell.

7. The polynucleotide of claim 6, wherein the 5' signal sequence portion encodes a signal polypeptide having an amino acid sequence selected from:
   (a) SEQ ID NO: 24;
   (b) variants of SEQ ID NO: 24, varying from the corresponding sequence by 1, 2 or 3 point mutations, amino acid insertions or amino acid deletions, which variants are capable of directing transport of said bacterial toxin polypeptide to the periplasm of said bacterial host cell; and
   (c) fragments of at least 10 amino acids of SEQ ID NO: 24, which fragments are capable of directing transport of said bacterial toxin polypeptide to the periplasm of said bacterial host cell.

8. The polynucleotide of claim 6 wherein the 5' signal sequence portion encodes a polypeptide selected from SEQ ID NO: 2, 4, 6, 8, 10, 12, 14, 16, 18, 20, 22, 24, and 26.

9. The polynucleotide of claim 6 wherein the 5' signal sequence portion encodes a polypeptide of SEQ ID NO: 24.

10. The polynucleotide of claim 6 wherein the 5' signal sequence portion comprises a nucleic acid sequence selected from SEQ ID NO: 1, 3, 5, 7, 9, 11, 13, 15, 17, 19, 21, 23, and 25.

11. The polynucleotide of claim 6 wherein the 5' signal sequence portion comprises SEQ ID NO: 23.

12. The polynucleotide of claim 6 wherein the 3' toxin portion encodes CRM197.

13. The polynucleotide of claim 6 wherein the 3' toxin portion encodes a polypeptide having at least 95% sequence identity to SEQ ID NO: 32.

14. The polynucleotide of claim 6 wherein the 3' toxin portion encodes a polypeptide having the amino acid sequence of SEQ ID NO: 32.

15. The polynucleotide of claim 6 wherein the 3' toxin portion comprises SEQ ID NO:31.

16. The polynucleotide of claim 6 which encodes a polypeptide comprising any one of SEQ ID NOs: 33-45.

17. The polynucleotide of claim 6 wherein the 5' signal sequence portion is directly 5' of the 3' toxin portion.

18. The polynucleotide of claim 1 wherein the 3' toxin portion encodes CRM197.

19. The polynucleotide of claim 1 wherein the 3' toxin portion encodes a polypeptide having at least 95% sequence identity to SEQ ID NO: 32.

20. The polynucleotide of claim 1 which encodes a polypeptide comprising any one of SEQ ID NOs: 33-45.

21. The polynucleotide of claim 1 wherein the 5' signal sequence portion is directly 5' of the 3' toxin portion.

* * * * *

SEQUENCE LISTING

<160> NUMBER OF SEQ ID NOS: 45

<210> SEQ ID NO 1
<211> LENGTH: 72
<212> TYPE: DNA
<213> ORGANISM: Artificial Sequence
<220> FEATURE:
<223> OTHER INFORMATION: PhtE signal sequence

<400> SEQUENCE: 1
atgaaattta gtaaaaaata tatagcagct ggatcagctg ttatcgtatc cttgagtcta    60
tgtgcctatg ca                                                        72

<210> SEQ ID NO 2
<211> LENGTH: 24
<212> TYPE: PRT
<213> ORGANISM: Artificial Sequence
<220> FEATURE:
<223> OTHER INFORMATION: PhtE signal sequence

<400> SEQUENCE: 2

Met Lys Phe Ser Lys Lys Tyr Ile Ala Ala Gly Ser Ala Val Ile Val
 1               5                  10                  15

Ser Leu Ser Leu Cys Ala Tyr Ala
            20

<210> SEQ ID NO 3
<211> LENGTH: 75
<212> TYPE: DNA
<213> ORGANISM: Artificial Sequence
<220> FEATURE:

<223> OTHER INFORMATION: SipA signal sequence

<400> SEQUENCE: 3
atgaaaatga ataaaaaggt actattgaca tcgacaatgg cagcttcgct attatcagtc    60
gcaagtgttc aagca    75

<210> SEQ ID NO 4
<211> LENGTH: 25
<212> TYPE: PRT
<213> ORGANISM: Artificial Sequence
<220> FEATURE:
<223> OTHER INFORMATION: SipA signal sequence

<400> SEQUENCE: 4

Met Lys Met Asn Lys Lys Val Leu Leu Thr Ser Thr Met Ala Ala Ser
1               5                   10                  15

Leu Leu Ser Val Ala Ser Val Gln Ala
            20                  25

<210> SEQ ID NO 5
<211> LENGTH: 63
<212> TYPE: DNA
<213> ORGANISM: Artificial Sequence
<220> FEATURE:
<223> OTHER INFORMATION: OmpA signal sequence

<400> SEQUENCE: 5
atgaaaaaga cagctatcgc gattgcagtg gcactggctg gtttcgctac cgtagcgcag    60
gcc    63

<210> SEQ ID NO 6
<211> LENGTH: 21
<212> TYPE: PRT
<213> ORGANISM: Artificial Sequence
<220> FEATURE:
<223> OTHER INFORMATION: OmpA signal sequence

<400> SEQUENCE: 6

Met Lys Lys Thr Ala Ile Ala Ile Ala Val Ala Leu Ala Gly Phe Ala
1               5                   10                  15

Thr Val Ala Gln Ala
            20

<210> SEQ ID NO 7
<211> LENGTH: 57
<212> TYPE: DNA
<213> ORGANISM: Artificial Sequence
<220> FEATURE:
<223> OTHER INFORMATION: NspA signal sequence

<400> SEQUENCE: 7
atgaaaaaag cacttgccac actgattgcc ctcgctctcc cggccgccgc actggcg    57

<210> SEQ ID NO 8
<211> LENGTH: 19
<212> TYPE: PRT
<213> ORGANISM: Artificial Sequence
<220> FEATURE:
<223> OTHER INFORMATION: NspA signal sequence

<400> SEQUENCE: 8

Met Lys Lys Ala Leu Ala Thr Leu Ile Ala Leu Ala Leu Pro Ala Ala
1               5                   10                  15

Ala Leu Ala

<210> SEQ ID NO 9
<211> LENGTH: 54
<212> TYPE: DNA
<213> ORGANISM: Artificial Sequence
<220> FEATURE:
<223> OTHER INFORMATION: TorT signal sequence

<400> SEQUENCE: 9
atgcgcgtac tgctattttt acttcttttcc cttttcatgt tgccggcatt ttcg      54

<210> SEQ ID NO 10
<211> LENGTH: 18
<212> TYPE: PRT
<213> ORGANISM: Artificial Sequence
<220> FEATURE:
<223> OTHER INFORMATION: TorT signal sequence

<400> SEQUENCE: 10

Met Arg Val Leu Leu Phe Leu Leu Leu Ser Leu Phe Met Leu Pro Ala
1               5                   10                  15

Phe Ser

<210> SEQ ID NO 11
<211> LENGTH: 69
<212> TYPE: DNA
<213> ORGANISM: Artificial Sequence
<220> FEATURE:
<223> OTHER INFORMATION: SfmC signal sequence

<400> SEQUENCE: 11
atgatgacta aaataaagtt attgatgctc attatatttt atttaatcat ttcggccagc      60
gcccatgct                                                              69

<210> SEQ ID NO 12
<211> LENGTH: 23
<212> TYPE: PRT
<213> ORGANISM: Artificial Sequence
<220> FEATURE:
<223> OTHER INFORMATION: SfmC signal sequence

<400> SEQUENCE: 12

Met Met Thr Lys Ile Lys Leu Leu Met Leu Ile Ile Phe Tyr Leu Ile
1               5                   10                  15

Ile Ser Ala Ser Ala His Ala
            20

<210> SEQ ID NO 13
<211> LENGTH: 75
<212> TYPE: DNA
<213> ORGANISM: Artificial Sequence
<220> FEATURE:
<223> OTHER INFORMATION: FocC signal sequence

<400> SEQUENCE: 13
atgatgaagc acatgcgtat atgggccgtt ctggcatcat ttttagtctt tttttatatt      60
ccgcagagct atgcc                                                      75

<210> SEQ ID NO 14
<211> LENGTH: 25
<212> TYPE: PRT
<213> ORGANISM: Artificial Sequence
<220> FEATURE:

<223> OTHER INFORMATION: FocC signal sequence

<400> SEQUENCE: 14

Met Met Lys His Met Arg Ile Trp Ala Val Leu Ala Ser Phe Leu Val
1               5                   10                  15

Phe Phe Tyr Ile Pro Gln Ser Tyr Ala
            20                  25

<210> SEQ ID NO 15
<211> LENGTH: 54
<212> TYPE: DNA
<213> ORGANISM: Artificial Sequence
<220> FEATURE:
<223> OTHER INFORMATION: CcmH signal sequence

<400> SEQUENCE: 15
atgaggtttt tattgggcgt gctgatgctg atgatctccg gctcagcgct ggcg        54

<210> SEQ ID NO 16
<211> LENGTH: 18
<212> TYPE: PRT
<213> ORGANISM: Artificial Sequence
<220> FEATURE:
<223> OTHER INFORMATION: CcmH signal sequence

<400> SEQUENCE: 16

Met Arg Phe Leu Leu Gly Val Leu Met Leu Met Ile Ser Gly Ser Ala
1               5                   10                  15

Leu Ala

<210> SEQ ID NO 17
<211> LENGTH: 69
<212> TYPE: DNA
<213> ORGANISM: Artificial Sequence
<220> FEATURE:
<223> OTHER INFORMATION: YraI signal sequence

<400> SEQUENCE: 17
atgtcaaaac gaacattcgc ggtgatatta accttgttgt gtagcttctg tattggccag    60
gcgcttgca                                                            69

<210> SEQ ID NO 18
<211> LENGTH: 23
<212> TYPE: PRT
<213> ORGANISM: Artificial Sequence
<220> FEATURE:
<223> OTHER INFORMATION: YraI signal sequence

<400> SEQUENCE: 18

Met Ser Lys Arg Thr Phe Ala Val Ile Leu Thr Leu Leu Cys Ser Phe
1               5                   10                  15

Cys Ile Gly Gln Ala Leu Ala
            20

<210> SEQ ID NO 19
<211> LENGTH: 66
<212> TYPE: DNA
<213> ORGANISM: Artificial Sequence
<220> FEATURE:
<223> OTHER INFORMATION: TolB signal sequence

<400> SEQUENCE: 19
atgatgaagc aggcattacg agtagcattt ggttttctca ctgtgtgggc atcagttctg    60
catgct 66

<210> SEQ ID NO 20
<211> LENGTH: 22
<212> TYPE: PRT
<213> ORGANISM: Artificial Sequence
<220> FEATURE:
<223> OTHER INFORMATION: TolB signal sequence

<400> SEQUENCE: 20

Met Met Lys Gln Ala Leu Arg Val Ala Phe Gly Phe Leu Ile Leu Trp
1               5                   10                  15

Ala Ser Val Leu His Ala
            20

<210> SEQ ID NO 21
<211> LENGTH: 66
<212> TYPE: DNA
<213> ORGANISM: Artificial Sequence
<220> FEATURE:
<223> OTHER INFORMATION: NikA signal sequence

<400> SEQUENCE: 21
atgctctcca cactccgccg cactctattt gcgctgctgg cttgtgcgtc ttttatcgtc    60
catgcc    66

<210> SEQ ID NO 22
<211> LENGTH: 22
<212> TYPE: PRT
<213> ORGANISM: Artificial Sequence
<220> FEATURE:
<223> OTHER INFORMATION: NikA signal sequence

<400> SEQUENCE: 22

Met Leu Ser Thr Leu Arg Arg Thr Leu Phe Ala Leu Leu Ala Cys Ala
1               5                   10                  15

Ser Phe Ile Val His Ala
            20

<210> SEQ ID NO 23
<211> LENGTH: 57
<212> TYPE: DNA
<213> ORGANISM: Artificial Sequence
<220> FEATURE:
<223> OTHER INFORMATION: FlgI signal sequence

<400> SEQUENCE: 23
atgattaaat ttctctctgc attaattctt ctactggtca cgacggcggc tcaggct    57

<210> SEQ ID NO 24
<211> LENGTH: 19
<212> TYPE: PRT
<213> ORGANISM: Artificial Sequence
<220> FEATURE:
<223> OTHER INFORMATION: FlgI signal sequence

<400> SEQUENCE: 24

Met Ile Lys Phe Leu Ser Ala Leu Ile Leu Leu Leu Val Thr Thr Ala
1               5                   10                  15

Ala Gln Ala

<210> SEQ ID NO 25
<211> LENGTH: 57
<212> TYPE: DNA

```
<213> ORGANISM: Artificial Sequence
<220> FEATURE:
<223> OTHER INFORMATION: DsbA signal sequence

<400> SEQUENCE: 25
atgaaaaaga tttggctggc gctggctggt ttagttttag cgtttagcgc atcggcg      57

<210> SEQ ID NO 26
<211> LENGTH: 19
<212> TYPE: PRT
<213> ORGANISM: Artificial Sequence
<220> FEATURE:
<223> OTHER INFORMATION: DsbA signal sequence

<400> SEQUENCE: 26

Met Lys Lys Ile Trp Leu Ala Leu Ala Gly Leu Val Leu Ala Phe Ser
 1               5                  10                  15

Ala Ser Ala

<210> SEQ ID NO 27
<211> LENGTH: 39
<212> TYPE: DNA
<213> ORGANISM: Artificial Sequence
<220> FEATURE:
<223> OTHER INFORMATION: Primer

<400> SEQUENCE: 27
gcgcggcata tgggtgcgga tgatgtggtg gatagcagc                           39

<210> SEQ ID NO 28
<211> LENGTH: 33
<212> TYPE: DNA
<213> ORGANISM: Artificial Sequence
<220> FEATURE:
<223> OTHER INFORMATION: Primer

<400> SEQUENCE: 28
gcggagctcg agttattagc ttttgatttc gaa                                 33

<210> SEQ ID NO 29
<211> LENGTH: 90
<212> TYPE: DNA
<213> ORGANISM: Artificial Sequence
<220> FEATURE:
<223> OTHER INFORMATION: Primer

<400> SEQUENCE: 29
ggagcgcata tgattaaatt tctctctgca ttaattcttc tactggtcac gacggcggct    60
caggctggtg cggatgatgt ggtggatagc                                     90

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
cacgccgcat agttcgcacc cgca                                           24

<210> SEQ ID NO 31
<211> LENGTH: 1605
<212> TYPE: DNA
<213> ORGANISM: C. diphtheriae mutant CRM197
```

<400> SEQUENCE: 31

```
ggtgcggatg atgtggtgga tagcagcaaa tcttttgtga tggaaaactt tagcagctat      60
catggcacca aaccgggcta tgtggatagc attcagaaag gcatccagaa accgaaaagc     120
ggcacccagg gcaactatga tgatgattgg aaagaatttt atagcaccga taacaaatat     180
gatgcggcgg gttatagcgt ggataacgaa atccgctgtc tggcaaaagc gggcggtgtg     240
gtgaaagtga cctatccggg cctgaccaaa gtgctggccc tgaaagtgga taacgcggaa     300
accatcaaaa aagaactggg cctgagcctg accgaaccgc tgatggaaca ggtgggcacc     360
gaagaattta ttaaacgctt tggcgatggc gcgagccgtg tggttctgag cctgccgttt     420
gcggaaggca gcagcagcgt ggaatatatt aacaactggg aacaggcgaa agccctgagc     480
gtggaactgg aaattaactt tgaaacccgt ggcaaacgtg ccaggatgc gatgtatgaa      540
tacatggcgc aggcgtgcgc gggcaatcgt gtgcgtcgta gcgtgggcag cagcctgagc     600
tgcattaacc tggattggga cgtcattcgt gataaaacca aaaccaaaat cgaaagcctg     660
aaagaacatg gcccgatcaa aaacaaaatg agcgaaagcc cgaacaaaac cgtgagcgaa     720
gaaaaagcga aacagtatct ggaagaattt catcagaccg cgctggaaca tccggaactg     780
agcgaactga aaaccgtgac cggcaccaat ccggtgtttg cgggtgcgaa ctatgcggcg     840
tgggcggtga atgtggcgca ggtgattgat agcgaaaccg cggataacct ggaaaaaacc     900
accgcggccc tgagcattct gccgggcatt ggcagcgtga tgggcattgc ggatggcgcg     960
gtgcatcata caccgaaga aattgtggcg cagagcattg ccctgagcag cctgatggtg    1020
gcgcaggcga ttccgctggt tggcgaactg gtggatattg gctttgcggc gtacaacttt    1080
gtggaaagca tcatcaacct gtttcaggtg gtgcataaca gctataaccg tccggcgtat    1140
tctccgggtc ataaaaccca gccgtttctg catgatggct atgcggtgag ctggaacacc    1200
gtggaagata gcattattcg taccggcttt cagggcgaaa gcggccatga tattaaaatt    1260
accgcggaaa acacccccgct gccgattgcg ggtgttctgc tgccgaccat tccgggcaaa    1320
ctggatgtga acaaaagcaa aacccatatt agcgtgaacg gtcgtaaaat tcgtatgcgt    1380
tgccgtgcga ttgatggcga tgtgaccttt tgccgtccga aaagcccggt gtatgtgggc    1440
aacggcgtgc acgcgaacct gcatgtggcg tttcatcgta gcagcagcga aaaaatccat    1500
agcaacgaaa ttagcagcga tagcattggc gtgctgggct atcagaaaac cgtggaccat    1560
accaaagtga actctaaact gagcctgttc ttcgaaatca aaagc                    1605
```

<210> SEQ ID NO 32
<211> LENGTH: 535
<212> TYPE: PRT
<213> ORGANISM: C. diphtheriae mutant CRM197

<400> SEQUENCE: 32

```
Gly Ala Asp Asp Val Val Asp Ser Ser Lys Ser Phe Val Met Glu Asn
 1               5                  10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80
```

```
Val Lys Val Thr Tyr Pro Gly Leu Thr Lys Val Leu Ala Leu Lys Val
                85              90              95

Asp Asn Ala Glu Thr Ile Lys Lys Glu Leu Gly Leu Ser Leu Thr Glu
            100             105             110

Pro Leu Met Glu Gln Val Gly Thr Glu Glu Phe Ile Lys Arg Phe Gly
            115             120             125

Asp Gly Ala Ser Arg Val Val Leu Ser Leu Pro Phe Ala Glu Gly Ser
            130             135             140

Ser Ser Val Glu Tyr Ile Asn Asn Trp Glu Gln Ala Lys Ala Leu Ser
145             150             155             160

Val Glu Leu Glu Ile Asn Phe Glu Thr Arg Gly Lys Arg Gly Gln Asp
                165             170             175

Ala Met Tyr Glu Tyr Met Ala Gln Ala Cys Ala Gly Asn Arg Val Arg
            180             185             190

Arg Ser Val Gly Ser Ser Leu Ser Cys Ile Asn Leu Asp Trp Asp Val
            195             200             205

Ile Arg Asp Lys Thr Lys Thr Lys Ile Glu Ser Leu Lys Glu His Gly
            210             215             220

Pro Ile Lys Asn Lys Met Ser Glu Ser Pro Asn Lys Thr Val Ser Glu
225             230             235             240

Glu Lys Ala Lys Gln Tyr Leu Glu Glu Phe His Gln Thr Ala Leu Glu
                245             250             255

His Pro Glu Leu Ser Glu Leu Lys Thr Val Thr Gly Thr Asn Pro Val
            260             265             270

Phe Ala Gly Ala Asn Tyr Ala Ala Trp Ala Val Asn Val Ala Gln Val
            275             280             285

Ile Asp Ser Glu Thr Ala Asp Asn Leu Glu Lys Thr Thr Ala Ala Leu
            290             295             300

Ser Ile Leu Pro Gly Ile Gly Ser Val Met Gly Ile Ala Asp Gly Ala
305             310             315             320

Val His His Asn Thr Glu Glu Ile Val Ala Gln Ser Ile Ala Leu Ser
                325             330             335

Ser Leu Met Val Ala Gln Ala Ile Pro Leu Val Gly Glu Leu Val Asp
            340             345             350

Ile Gly Phe Ala Ala Tyr Asn Phe Val Glu Ser Ile Ile Asn Leu Phe
            355             360             365

Gln Val Val His Asn Ser Tyr Asn Arg Pro Ala Tyr Ser Pro Gly His
            370             375             380

Lys Thr Gln Pro Phe Leu His Asp Gly Tyr Ala Val Ser Trp Asn Thr
385             390             395             400

Val Glu Asp Ser Ile Ile Arg Thr Gly Phe Gln Gly Glu Ser Gly His
                405             410             415

Asp Ile Lys Ile Thr Ala Glu Asn Thr Pro Leu Pro Ile Ala Gly Val
            420             425             430

Leu Leu Pro Thr Ile Pro Gly Lys Leu Asp Val Asn Lys Ser Lys Thr
            435             440             445

His Ile Ser Val Asn Gly Arg Lys Ile Arg Met Arg Cys Arg Ala Ile
            450             455             460

Asp Gly Asp Val Thr Phe Cys Arg Pro Lys Ser Pro Val Tyr Val Gly
465             470             475             480

Asn Gly Val His Ala Asn Leu His Val Ala Phe His Arg Ser Ser Ser
                485             490             495

Glu Lys Ile His Ser Asn Glu Ile Ser Ser Asp Ser Ile Gly Val Leu
```

```
                500               505               510
Gly Tyr Gln Lys Thr Val Asp His Thr Lys Val Asn Ser Lys Leu Ser
            515                 520                 525

Leu Phe Phe Glu Ile Lys Ser
        530             535

<210> SEQ ID NO 33
<211> LENGTH: 54
<212> TYPE: PRT
<213> ORGANISM: Artificial Sequence
<220> FEATURE:
<223> OTHER INFORMATION: PhtE signal sequence and the first 30 amino
      acids of CRM197

<400> SEQUENCE: 33

Met Lys Phe Ser Lys Lys Tyr Ile Ala Ala Gly Ser Ala Val Ile Val
1               5                   10                  15

Ser Leu Ser Leu Cys Ala Tyr Ala Gly Ala Asp Asp Val Val Asp Ser
            20                  25                  30

Ser Lys Ser Phe Val Met Glu Asn Phe Ser Ser Tyr His Gly Thr Lys
        35                  40                  45

Pro Gly Tyr Val Asp Ser
    50

<210> SEQ ID NO 34
<211> LENGTH: 55
<212> TYPE: PRT
<213> ORGANISM: Artificial Sequence
<220> FEATURE:
<223> OTHER INFORMATION: SipA signal sequence and the first 30 amino
      acids of CRM197

<400> SEQUENCE: 34

Met Lys Met Asn Lys Lys Val Leu Leu Thr Ser Thr Met Ala Ala Ser
1               5                   10                  15

Leu Leu Ser Val Ala Ser Val Gln Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser
    50                  55

<210> SEQ ID NO 35
<211> LENGTH: 51
<212> TYPE: PRT
<213> ORGANISM: Artificial Sequence
<220> FEATURE:
<223> OTHER INFORMATION: OmpA signal sequence and the first 30 amino
      acids of CRM197

<400> SEQUENCE: 35

Met Lys Lys Thr Ala Ile Ala Ile Ala Val Ala Leu Ala Gly Phe Ala
1               5                   10                  15

Thr Val Ala Gln Ala Gly Ala Asp Asp Val Val Asp Ser Ser Lys Ser
            20                  25                  30

Phe Val Met Glu Asn Phe Ser Ser Tyr His Gly Thr Lys Pro Gly Tyr
        35                  40                  45

Val Asp Ser
    50

<210> SEQ ID NO 36
```

```
<211> LENGTH: 49
<212> TYPE: PRT
<213> ORGANISM: Artificial Sequence
<220> FEATURE:
<223> OTHER INFORMATION: NspA signal sequence and the first 30 amino
      acids of CRM197

<400> SEQUENCE: 36

Met Lys Lys Ala Leu Ala Thr Leu Ile Ala Leu Ala Leu Pro Ala Ala
1               5                   10                  15

Ala Leu Ala Gly Ala Asp Asp Val Val Asp Ser Ser Lys Ser Phe Val
            20                  25                  30

Met Glu Asn Phe Ser Ser Tyr His Gly Thr Lys Pro Gly Tyr Val Asp
        35                  40                  45

Ser

<210> SEQ ID NO 37
<211> LENGTH: 48
<212> TYPE: PRT
<213> ORGANISM: Artificial Sequence
<220> FEATURE:
<223> OTHER INFORMATION: TorT signal sequence and the first 30 amino
      acids of CRM197

<400> SEQUENCE: 37

Met Arg Val Leu Leu Phe Leu Leu Leu Ser Leu Phe Met Leu Pro Ala
1               5                   10                  15

Phe Ser Gly Ala Asp Asp Val Val Asp Ser Ser Lys Ser Phe Val Met
            20                  25                  30

Glu Asn Phe Ser Ser Tyr His Gly Thr Lys Pro Gly Tyr Val Asp Ser
        35                  40                  45

<210> SEQ ID NO 38
<211> LENGTH: 53
<212> TYPE: PRT
<213> ORGANISM: Artificial Sequence
<220> FEATURE:
<223> OTHER INFORMATION: SfmC signal sequence and the first 30 amino
      acids of CRM197

<400> SEQUENCE: 38

Met Met Thr Lys Ile Lys Leu Leu Met Leu Ile Ile Phe Tyr Leu Ile
1               5                   10                  15

Ile Ser Ala Ser Ala His Ala Gly Ala Asp Asp Val Val Asp Ser Ser
            20                  25                  30

Lys Ser Phe Val Met Glu Asn Phe Ser Ser Tyr His Gly Thr Lys Pro
        35                  40                  45

Gly Tyr Val Asp Ser
    50

<210> SEQ ID NO 39
<211> LENGTH: 55
<212> TYPE: PRT
<213> ORGANISM: Artificial Sequence
<220> FEATURE:
<223> OTHER INFORMATION: FocC signal sequence and the first 30 amino
      acids of CRM197

<400> SEQUENCE: 39

Met Met Lys His Met Arg Ile Trp Ala Val Leu Ala Ser Phe Leu Val
1               5                   10                  15

Phe Phe Tyr Ile Pro Gln Ser Tyr Ala Gly Ala Asp Asp Val Val Asp
            20                  25                  30
```

Ser Ser Lys Ser Phe Val Met Glu Asn Phe Ser Ser Tyr His Gly Thr
        35                  40                  45

Lys Pro Gly Tyr Val Asp Ser
    50                  55

<210> SEQ ID NO 40
<211> LENGTH: 48
<212> TYPE: PRT
<213> ORGANISM: Artificial Sequence
<220> FEATURE:
<223> OTHER INFORMATION: CcmH signal sequence and the first 30 amino
      acids of CRM197

<400> SEQUENCE: 40

Met Arg Phe Leu Leu Gly Val Leu Met Leu Met Ile Ser Gly Ser Ala
1               5                   10                  15

Leu Ala Gly Ala Asp Asp Val Val Asp Ser Ser Lys Ser Phe Val Met
                20                  25                  30

Glu Asn Phe Ser Ser Tyr His Gly Thr Lys Pro Gly Tyr Val Asp Ser
            35                  40                  45

<210> SEQ ID NO 41
<211> LENGTH: 53
<212> TYPE: PRT
<213> ORGANISM: Artificial Sequence
<220> FEATURE:
<223> OTHER INFORMATION: YraI signal sequence and the first 30 amino
      acids of CRM197

<400> SEQUENCE: 41

Met Ser Lys Arg Thr Phe Ala Val Ile Leu Thr Leu Leu Cys Ser Phe
1               5                   10                  15

Cys Ile Gly Gln Ala Leu Ala Gly Ala Asp Asp Val Val Asp Ser Ser
                20                  25                  30

Lys Ser Phe Val Met Glu Asn Phe Ser Ser Tyr His Gly Thr Lys Pro
            35                  40                  45

Gly Tyr Val Asp Ser
    50

<210> SEQ ID NO 42
<211> LENGTH: 52
<212> TYPE: PRT
<213> ORGANISM: Artificial Sequence
<220> FEATURE:
<223> OTHER INFORMATION: TolB signal sequence and the first 30 amino
      acids of CRM197

<400> SEQUENCE: 42

Met Met Lys Gln Ala Leu Arg Val Ala Phe Gly Phe Leu Ile Leu Trp
1               5                   10                  15

Ala Ser Val Leu His Ala Gly Ala Asp Asp Val Val Asp Ser Ser Lys
                20                  25                  30

Ser Phe Val Met Glu Asn Phe Ser Ser Tyr His Gly Thr Lys Pro Gly
            35                  40                  45

Tyr Val Asp Ser
    50

<210> SEQ ID NO 43
<211> LENGTH: 52
<212> TYPE: PRT
<213> ORGANISM: Artificial Sequence
<220> FEATURE:

```
<223> OTHER INFORMATION: NikA signal sequence and the first 30 amino
      acids of CRM197

<400> SEQUENCE: 43

Met Leu Ser Thr Leu Arg Arg Thr Leu Phe Ala Leu Leu Ala Cys Ala
 1               5                  10                  15

Ser Phe Ile Val His Ala Gly Ala Asp Asp Val Val Asp Ser Ser Lys
                20                  25                  30

Ser Phe Val Met Glu Asn Phe Ser Ser Tyr His Gly Thr Lys Pro Gly
            35                  40                  45

Tyr Val Asp Ser
     50

<210> SEQ ID NO 44
<211> LENGTH: 49
<212> TYPE: PRT
<213> ORGANISM: Artificial Sequence
<220> FEATURE:
<223> OTHER INFORMATION: FlgI signal sequence and the first 30 amino
      acids of CRM197

<400> SEQUENCE: 44

Met Ile Lys Phe Leu Ser Ala Leu Ile Leu Leu Leu Val Thr Thr Ala
 1               5                  10                  15

Ala Gln Ala Gly Ala Asp Asp Val Val Asp Ser Ser Lys Ser Phe Val
                20                  25                  30

Met Glu Asn Phe Ser Ser Tyr His Gly Thr Lys Pro Gly Tyr Val Asp
            35                  40                  45

Ser

<210> SEQ ID NO 45
<211> LENGTH: 49
<212> TYPE: PRT
<213> ORGANISM: Artificial Sequence
<220> FEATURE:
<223> OTHER INFORMATION: DsbA signal sequence and the first 30 amino
      acids of CRM197

<400> SEQUENCE: 45

Met Lys Lys Ile Trp Leu Ala Leu Ala Gly Leu Val Leu Ala Phe Ser
 1               5                  10                  15

Ala Ser Ala Gly Ala Asp Asp Val Val Asp Ser Ser Lys Ser Phe Val
                20                  25                  30

Met Glu Asn Phe Ser Ser Tyr His Gly Thr Lys Pro Gly Tyr Val Asp
            35                  40                  45

Ser
```